USO09259491B2

United States Patent
Beltrami et al.

(10) Patent No.: US 9,259,491 B2
(45) Date of Patent: Feb. 16, 2016

(54) CLASS OF DIAZEPINE DERIVATIVE CHELATING AGENTS AND COMPLEXES WITH PARAMAGNETIC METALS THEREOF AS MRI CONTRAST AGENTS

(71) Applicant: BRACCO IMAGING S.P.A., Milan (IT)

(72) Inventors: Lorena Beltrami, Biella (IT); Luciano Lattuada, Bussero (IT); Alessandro Maiocchi, Monza (IT); Massimo Visigalli, Settala (IT); Loredana Sini, Orgosolo (IT)

(73) Assignee: Bracco Imaging S.P.A., Milan (IT)

( * ) Notice: Subject to any disclaimer, the term of this patent is extended or adjusted under 35 U.S.C. 154(b) by 0 days.

(21) Appl. No.: 14/384,414

(22) PCT Filed: Mar. 13, 2013

(86) PCT No.: PCT/EP2013/055094
§ 371 (c)(1),
(2) Date: Sep. 11, 2014

(87) PCT Pub. No.: WO2013/135750
PCT Pub. Date: Sep. 19, 2013

(65) Prior Publication Data
US 2015/0037261 A1    Feb. 5, 2015

(30) Foreign Application Priority Data
Mar. 14, 2012  (EP) ..................................... 12159378

(51) Int. Cl.
C07D 243/08    (2006.01)
C07F 9/645    (2006.01)
A61K 49/10    (2006.01)

(52) U.S. Cl.
CPC ............ A61K 49/106 (2013.01); C07D 243/08 (2013.01); C07F 9/645 (2013.01)

(58) Field of Classification Search
CPC ..... A61K 49/106; C07D 243/08; C07F 9/645
See application file for complete search history.

(56) References Cited

U.S. PATENT DOCUMENTS

| 2006/0018830 A1 | 1/2006 | Cappelletti et al. |
| 2006/0034773 A1* | 2/2006 | Giovenzana et al. ...... 424/9.361 |
| 2007/0258905 A1* | 11/2007 | Aime et al. .................. 424/9.36 |

FOREIGN PATENT DOCUMENTS

| EP | 0292689 A2 | 11/1988 |
| WO | 97-00087 A1 | 1/1997 |
| WO | 00-30688 A2 | 6/2000 |
| WO | 03-008390 A1 | 1/2003 |
| WO | 2006-136564 A1 | 12/2006 |

OTHER PUBLICATIONS

Caravan, Peter et al., "Gadolinium(III) Chelates as MRI Contrast Agents: Structure, Dynamics, and Applications", Chem. Rev., vol. 99, No. 9, 1999, pp. 2293-2352.
Editors: Merbach, Andre E. et al., "The Chemistry of Contrast Agents in Medical Magnetic Resonance Imaging", Chapter 2, John Wiley & Sons, Ltd, Chichester, England, 2001, pp. 45-119.
Editors: Greene-Theodora W. et al., "Protective Groups in Organic Synthesis", Chapter 5, 3rd Ed., Wiley Interscience, John Wiley & Sons, Inc., Canada, 1999, pp. 369-453.
PCT International Search Report for PCT/EP2013/055094, mail date May 17, 2012.
PCT Written Opinion for PCT/EP2013/055094, mail date May 17, 2012.
PCT International Preliminary Report on Patentability for PCT/EP2013/055094, mail date Sep. 25, 2014.

* cited by examiner

*Primary Examiner* — Valerie Rodriguez-Garcia
(74) *Attorney, Agent, or Firm* — VIVICAR Law, PLLC

(57) ABSTRACT

The present invention relates to a new class of diazepine-derivatives as chelating agents for paramagnetic metal ions, the process for their preparation, and use of such paramagnetic complexes as contrast agents, particularly suitable for Magnetic Resonance Imaging (MRI) analysis. The present invention refers to a new class of derivatives of formula (I), or a pharmaceutically acceptable salt thereof.

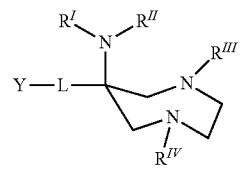

18 Claims, No Drawings

CLASS OF DIAZEPINE DERIVATIVE CHELATING AGENTS AND COMPLEXES WITH PARAMAGNETIC METALS THEREOF AS MRI CONTRAST AGENTS

CROSS-REFERENCE TO RELATED APPLICATIONS

This application is the national stage application of corresponding international application number PCT/EP2013/055094, filed Mar. 13, 2013, which claims priority to and the benefit of European application no. 12159378.4, filed Mar. 14, 2012, all of which are hereby incorporated by reference in their entirety.

FIELD OF THE INVENTION

The present invention relates to a new class of amphiphilic compounds with a diazepine-derivative as paramagnetic metal ion chelating unit and their use as MRI contrast agents.

STATE OF THE ART

A variety of chelating agents in the form of complex with metal ions are known in the art, for the use as contrast agent, particularly as MRI (magnetic resonance imaging) contrast agents, whereby the metal ion is a paramagnetic metal ion (see e.g. EP0292689). Said complexes are characterised by peculiar values of relaxivity (r1). The relaxivity is an intrinsic property of the paramagnetic complexes, useful to predict their ability to increase the nuclear magnetic relaxation rate of vicinal water protons. It has been observed, in fact, that the higher the relaxation rates, the more enhanced the contrast imaging properties of the compounds are. In particular, it is convenient to obtain high relaxivity values in order to get physiological information in a short frame of time, with advantages in terms of both image quality and clearance of the patient (see as general references: "The Chemistry of Contrast Agents in Medical Magnetic Resonance Imaging" Merbach et al, Eds. John Wiley and sons, Chichester, 2011 and Caravan P. et al, *Chem. Rev.* 1999, 99, 2293-2352).

WO00/30688 discloses a class of amphipatic polyaminopolycarboxylic chelating agents and paramagnetic metal complexes thereof as MRI contrast agents, particularly useful for the blood pool imaging, characterised in having a tetra-aza cyclic or a tri-aza linear backbone.

WO03/008390 generally refers to a series of multidentate aza ligands, either linear or cyclic, variously functionalised and able to complex a paramagnetic metal ions such as $Fe^{2+}$, $Gd^{3+}$ or $Mn^{2+}$.

Despite the potentiality of the chelating derivatives of the prior art in the complexation of paramagnetic metal ions for the use as MRI agents, there is still the need of a new class of chelating agents, able to form paramagnetic complexes, and also showing a favourable lasting activity and stability. Unexpectedly we have now found a new class of diazepine derivatives useful for the preparation of the corresponding paramagnetic complexes, showing a high relaxivity and also high stability, for the use in magnetic resonance imaging (MRI) techniques.

SUMMARY OF THE INVENTION

The present invention refers to a new class of derivatives of formula (I), or a pharmaceutically acceptable salt thereof:

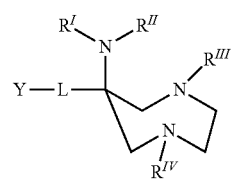

(I)

wherein:
Y is a group of formula: Y'—NH— or (Y')$_2$—N—, wherein Y' is the same or different and is selected from the group consisting of: a linear or branched saturated or unsaturated $C_1$-$C_{20}$ alkyl group; a $C_1$-$C_{10}$ alkyl group interrupted by one or more atom or group selected from: —P—, —O— (HO—P=O)—O— and optionally substituted by one or more group selected from: hydroxy —OH, carboxy —COOR1, oxycarbonyl-($C_1$-$C_{30}$)alkyl and oxycarbonyl-($C_2$-$C_{30}$)alkenyl group, wherein R1 is selected from: hydrogen H and a linear or branched $C_1$-$C_{10}$ alkyl group;

L is a bivalent linker selected from: aliphatic $C_3$-$C_{10}$ cyclic or heterocylic ring, linear or branched $C_1$-$C_6$ alkyl group and $C_2$-$C_6$ alkenyl or alkynyl group, optionally substituted or interrupted by a group or atom selected from: carbonyl —C=O, thiocarbonyl —C=S, amino —NR$_1$—, carboxy —COO—, oxy-carbonyl —OCO—, amido —NR1CO— or —CONR$_1$—, oxygen —O— and sulphur —S—, wherein R$_1$ is as above defined;

$R^{I-IV}$ are each independently selected from: hydrogen H, carboxy —COOR$_1$ and —($C_1$-$C_6$)alkylcarboxy group, wherein R$_1$ is as above defined.

In a further aspect, the invention provides a process for the preparation of the present compounds of formula (I) or a pharmaceutical acceptable salt thereof:

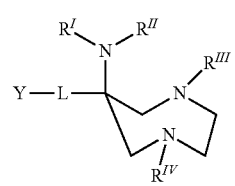

(I)

comprising the steps of:
a) preparation of a compound of formula:

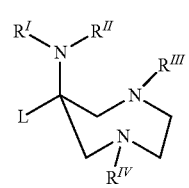

wherein $R^{I-IV}$ are as above defined and L is the linker comprising a terminal carboxylic function,
b) activation of said terminal carboxylic function of the linker, c) amidation reaction between the product of step b) and the Y group as herein defined;

d) cleavage of any protecting group to give the derivative of formula (I); and optionally e) chelation with a paramagnetic metal ion, to give the derivative of formula (I) in the form of a paramagnetic complex.

According to another aspect, the invention refers to a derivative of formula (I) in the form of a complex with a paramagnetic metal ion, useful as contrast agent for MRI analysis.

It is a further aspect of the invention a pharmaceutically acceptable composition comprising a chelate derivative of formula (I), or a pharmaceutical salt thereof, in the form of a complex with a paramagnetic metal ion in admixture with one or more physiologically acceptable carriers or excipients.

Said compositions are useful in particular as MRI contrast agent e.g. as blood pool agents, for the imaging of blood micro circulation in tumour or as contrast agent for angiography.

The present compositions are used in a method for imaging body regions comprising administering to a subject to be imaged a diagnostically effective amount of the composition of the invention.

Therefore, in another aspect, the present invention refers to a method for operating an imaging system, preferably MRI system, comprising the steps of:

a) submitting a subject pre-treated with a composition of the invention, and positioned in said imaging system, to a radiation frequency selected to interact with the active substrate of said composition; and b) recording a signal from said interaction.

In another embodiment, the present invention refers to a method of diagnosis comprising the administration of an effective dose of a composition of the invention to the human or animal body, examining the body with a diagnostic device and compiling data from the examination. In a preferred embodiment, said method of diagnosis is a MRI method.

DETAILED DESCRIPTION OF THE INVENTION

Term Definitions

Unless otherwise provided, the term linear or branched $C_1$-$C_6$ alkyl group means a linear or branched chain comprising from 1 to 6 carbon atoms such as: methyl, ethyl, propyl, iso-propyl, butyl, iso-butyl, tert-butyl, pentyl, hexyl and the like.

Similarly, the terms linear or branched $C_1$-$C_{10}$ and $C_1$-$C_{20}$ alkyl group mean a linear or branched chain comprising from 1 to 10 or from 1 to 20 carbon atoms, whereas the term $C_1$-$C_{30}$ alkyl group means a linear or branched chain comprising from 1 to 30 carbon atoms.

The term aliphatic $C_3$-$C_{10}$ cyclic or heterocyclic group optionally substituted means a carbon cyclic ring having from 3 to 10 carbon atoms, optionally interrupted by one or more heteroatoms such as: N, S, or O. Such aliphatic cyclic groups can be isolated (i.e. not embedded in other rings) or fused to one or more ring to constitute a polycyclic moiety. Unless otherwise provided, it should be noted that any heteroatom with free unsatisfied valences is assumed to have hydrogen atom to fulfil the valences. Non limiting examples of aliphatic $C_3$-$C_{10}$ cyclic groups are: cyclopropane, cyclobutane, cyclopentane, cyclohexane and the like. Non limiting examples of aliphatic $C_3$-$C_{10}$ heterocyclic groups are: pyrrolidine, piperidine, dioxane, and the like.

The term aromatic $C_6$-$C_{10}$ cyclic or heterocyclic group optionally substituted means an aromatic carbon cyclic ring having from 6 to 10 carbon atoms, optionally interrupted by one or more heteroatoms such as: N, O or S. Such aliphatic cyclic groups can be isolated (i.e. not embedded in other rings) or fused to one or more ring to constitute a polycyclic moiety. Non limiting examples of aromatic $C_6$-$C_{10}$ cyclic groups are: benzene, toluene, xylene, naphthalene, and the like.

Non limiting examples of aromatic $C_6$-$C_{10}$ heterocyclic groups are: pyridine, piperazine, thiophene, imidazole, pyrazole, pyrrole, furane, indole and the like.

The term oxycarbonyl-($C_1$-$C_{30}$)alkyl means a group of formula —O(CO)—($C_1$-$C_{30}$)alkyl, wherein ($C_1$-$C_{30}$)alkyl is as above defined.

The term —($C_1$-$C_6$)alkylcarboxy group means a group wherein a divalent ($C_1$-$C_6$)alkyl group is bonded to a carboxylic group of formula —COOR$_1$, wherein R$_1$ is as above defined.

The term "pharmaceutical acceptable" as used herein means that the carrier, diluent excipients and/or salt should be compatible with the other ingredients of the formulation.

The term "complex" or "paramagnetic complex" comprises within its meaning an adduct between a chelating moiety or ligand and a metal or paramagnetic metal ion respectively. The chelating moiety comprises at least one donor atom bound to the central metal ion.

Unless stated otherwise, a formula with chemical bonds shown as solid lines and not as wedges or dashed lines contemplates each possible isomer, e.g. each enantiomer and diastereoisomer, and a mixture of isomers such as racemic mixture. The compounds herein described can contain one or more asymmetric centres and thus potentially give rise to diastereoisomers and optical isomers. Unless stated to the contrary, the present invention includes all such possible diastereoisomer as well as their racemic mixtures, their substantially pure resolved enantiomers, all possible geometric isomers, and pharmaceutical acceptable salts thereof.

DESCRIPTION OF THE INVENTION

In a first aspect, the present invention refers to a new class of derivatives of Formula (I), or a pharmaceutical acceptable salt thereof:

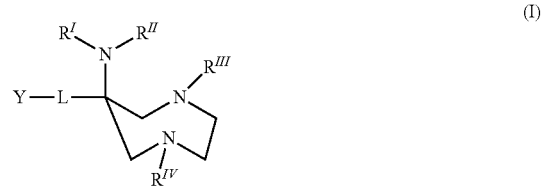

(I)

wherein:
Y is a group of formula: Y'—NH— or (Y')$_2$—N—, wherein Y' is, preferably the same, a linear or branched $C_1$-$C_{20}$ alkyl group, a $C_1$-$C_{10}$ alkyl group interrupted by —P— or —O— (HO—P═O)—O and optionally substituted by hydroxy —OH, carboxy —COOR$_1$, oxycarbonyl-($C_1$-$C_{30}$)alkyl or oxycarbonyl-($C_2$-$C_{30}$)alkenyl group.

According to Formula I, the derivatives of the invention comprise up to 2 residues Y' linked to the linker moiety L, preferably via an amidic function formed by the nitrogen atom of the Y group and a terminal carbonyl (—C═O) or thiocarbonyl (—C=S) function present at least at one end of the selected linker L as below described.

In a preferred embodiment, the Y group has the formula:

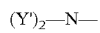

wherein preferred Y' residues are the same and are selected in the group consisting of: a $C_1$-$C_2$ alkyl chain, preferably a $C_2$-$C_{15}$ alkyl chain, even more preferably selected from: $C_4H_9$, $C_6H_{13}$, $C_8H_{17}$, $C_{10}H_{21}$ and $C_{12}H_{25}$. Accordingly, preferred Y groups have the formulae:

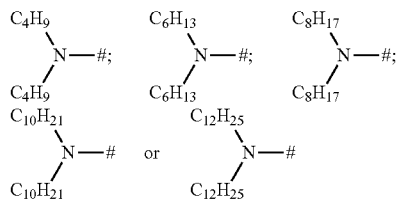

wherein # indicated the point of attachment to the linker L, the latter as defined below.

Equally preferred are derivatives of formula (I) of the invention, wherein Y has the formula:

and wherein Y', is an optionally substituted $C_1$-$C_{10}$ alkyl group, more preferably a $C_2$-$C_6$ alkyl group, interrupted by one or more group of formula:

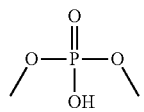

Even more preferably, Y has the formula: Y'—NH—, wherein Y' is a linear alkyl group having 4 to 6 carbon atoms, interrupted by one or more group of formula:

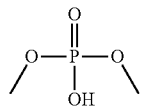

Also preferably Y is a phospholipid having the formula: Y'—NH— wherein Y' is a $C_2$-$C_6$ alkyl group, interrupted by one or more group of formula:

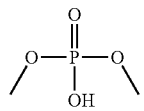

further substituted with at least one, preferably 2 or even 3, carboxyalkyl group(s) having from 9 to 20 carbon atoms, even more preferably from 8 to 18. It follows that Y can also be a monophosphate ester of a substituted or partially substituted glycerol, having at least one functional group of said glycerol esterified by a saturated or unsaturated aliphatic fatty acid, and the other two functions of the phosphoric acid being either free or in the form of a salt with an alkaline or earth-alkaline metal.

In a more preferred embodiment, Y is selected from:

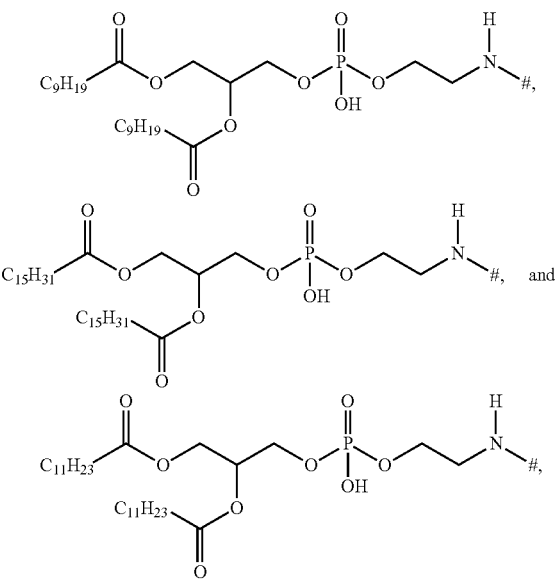

wherein # indicated the point of attachment to the linker L, the latter as herein defined.

According to a further embodiment, within the new class of derivatives of formula (I) of the present invention, the linker L is a divalent group which connects the diazepine moiety to the Y group, thus providing a proper distance that can be suitably selected.

In a preferred embodiment, the linker L is an optionally substituted linear or branched $C_1$-$C_6$ alkyl or $C_2$-$C_6$ alkenyl or alkynyl group, or a $C_3$-$C_8$ cyclic group, preferably, functionalised at one terminal side with a thiocarbonyl group (—C=S), or more preferably with a carbonyl group (—C=O) as the connection point with the terminal nitrogen atom of the Y residue in the derivatives of formula (I) of the present invention.

In further preferred embodiments, the linker L is a carbonyl-alkyl derivative selected from: an optionally substituted $C_1$-$C_6$ linear alkyl group derivative and a cycloalkyl $C_6$-$C_8$ residue, having a carbonyl function at the terminal side connected to the Y group. Examples of preferred linkers L are: methylcarbonyl, ethylcarbonyl, propylcarbonyl, butylcarbonyl, pentylcarbonyl and linear or cyclic hexylcarbonyl. Even more preferably, the linker L is selected from:
butyl carbonyl of formula:

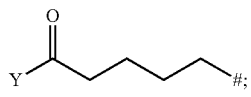

and
Cyclohexyl carbonyl of formula:

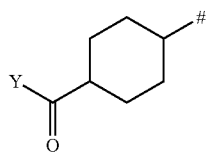

wherein # indicates the point of attachment to the diazepine core of the derivative of formula (I) of the invention.

As formerly indicated, the linker L is bound at one side to the Y group, and on the other side to the diazepine core. As shown above, the Y group of formula Y'—NH— or (Y')$_2$—N— presents a terminal nitrogen atom and preferably, the linker L is bound to Y through the secondary —NH— nitrogen atom, or equally preferably, via the tertiary —N— nitrogen atom, as part of an amidic functionality.

In this respect, preferred L-Y— systems are selected from:

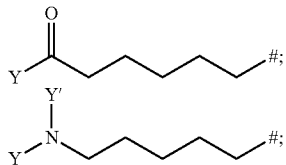

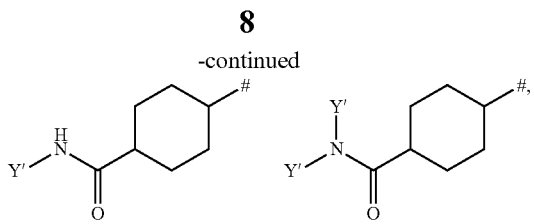

wherein Y' is as described above in any one of the preferred embodiments and # indicates the point of attachment to the diazepine core of the derivative of formula (I) of the invention.

In an even more preferred embodiment, the present invention refers to a new class of derivatives and pharmaceutical acceptable salts thereof, according to a formula (I) and selected from the group consisting of:

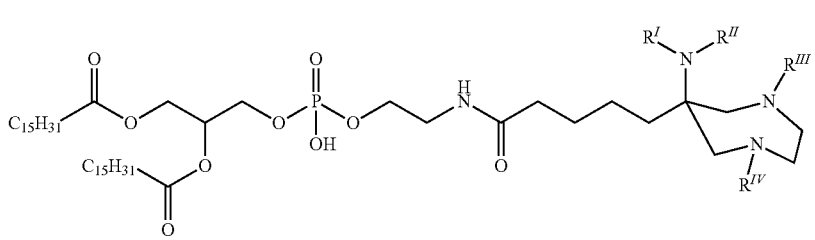

(II)

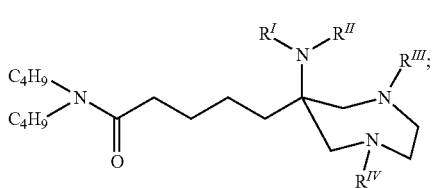

(III)

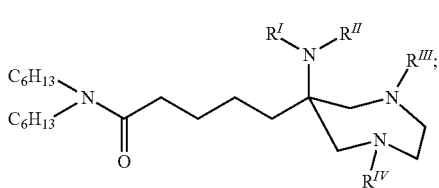

(IV)

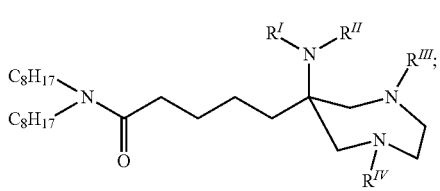

(V)

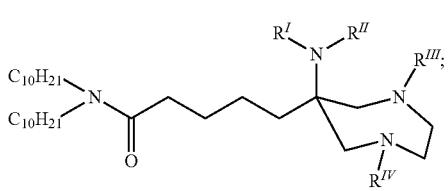

(VI)

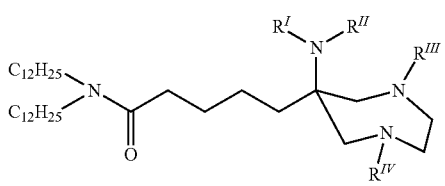

(VII)

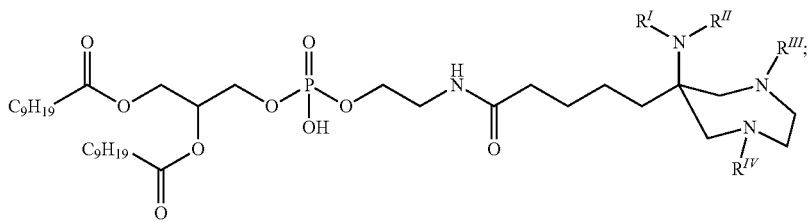

(VIII)

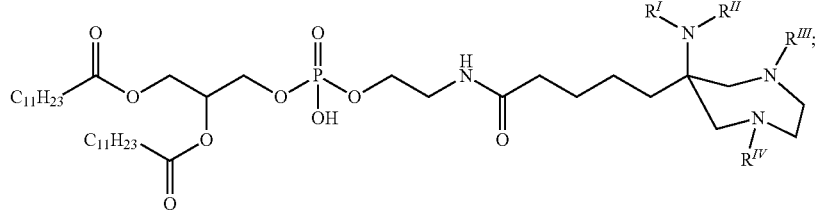 (IX)

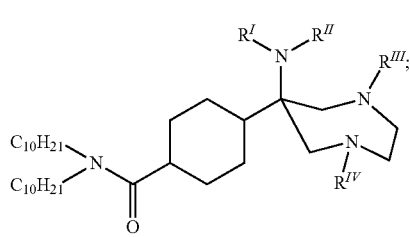 (X)

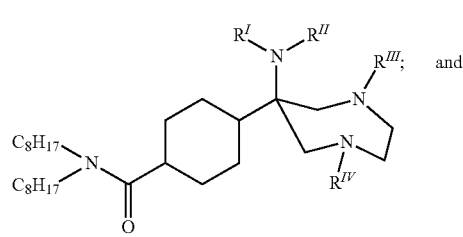 (XI) and

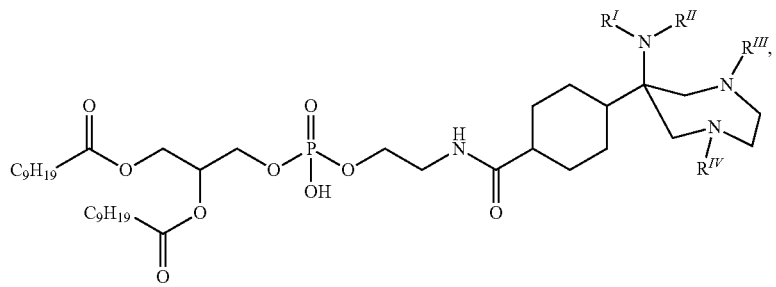 (XII)

wherein $R^{I-IV}$ are as herein defined.

In the class of derivatives of formula (I) of the invention, and according to any one of the above preferred embodiment, the groups $R^I$, $R^{II}$, $R^{III}$ and $R^{IV}$ are preferably a carboxylic derivative or a salt thereof, e.g. groups of formula:

—$R_2$—$COOR_1$ or —$R_2$—$COO^-M^+$ wherein $R_2$ is a bond or a $C_1$-$C_6$ alkyl residue, $R_1$ is as above defined, preferably hydrogen, and $M^+$ is a counterion, e.g. a metal ion.

In a further embodiment, the $R_2$ group is a bivalent radical selected from: methylene, ethylene, propylene and butylene, being methylene more preferred. In a still preferred embodiment, the groups $R^{I-IV}$ are, the same, a carboxymethyl group of formula —$CH_2$—$COOH$ or —$R_2$—$COO^-M^+$ as formerly defined, whereby, preferred compounds of formula (I) of the invention have the following general formula (I'):

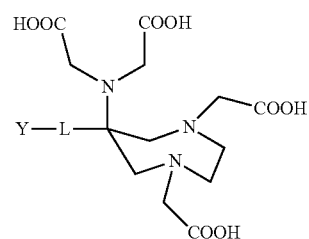 (I')

or a salt thereof, wherein, Y and L are as above described, also according to any one of the preferred embodiment. Preferred compounds of formula (I) according to the invention are selected from:

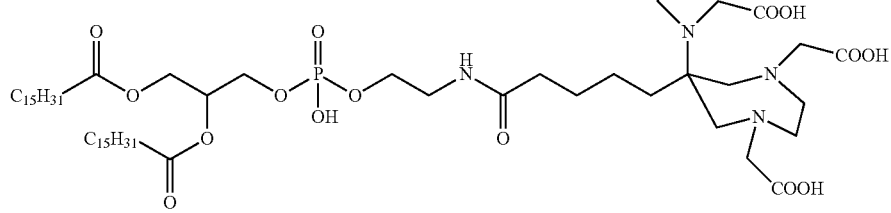

8d

-continued
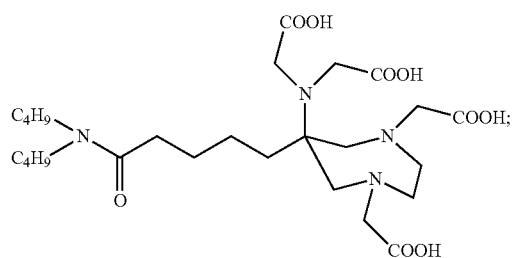
11a
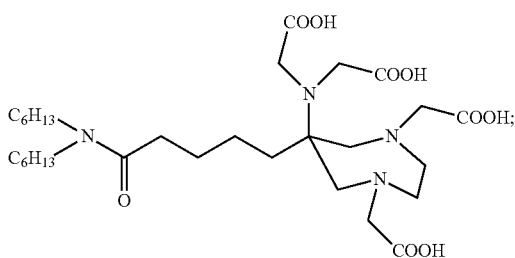
11b
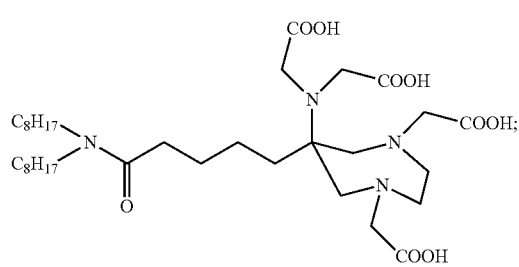
11c
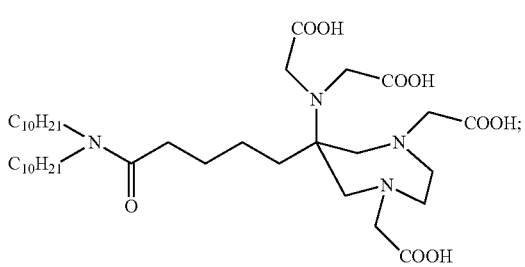
11d
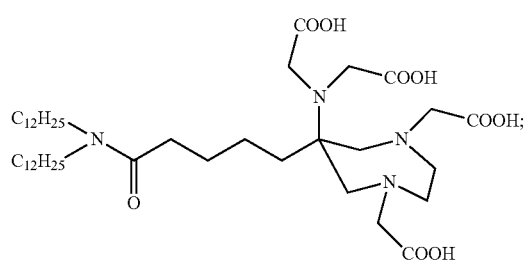
11e
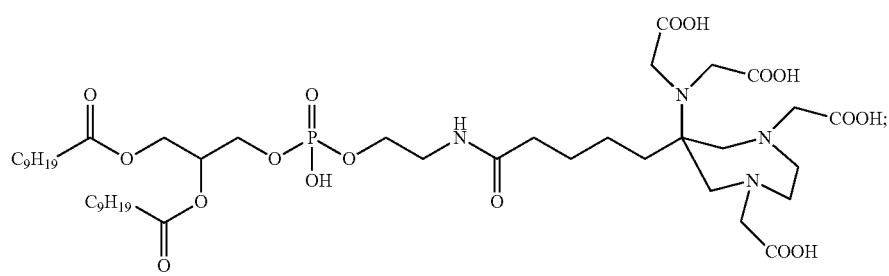
8b
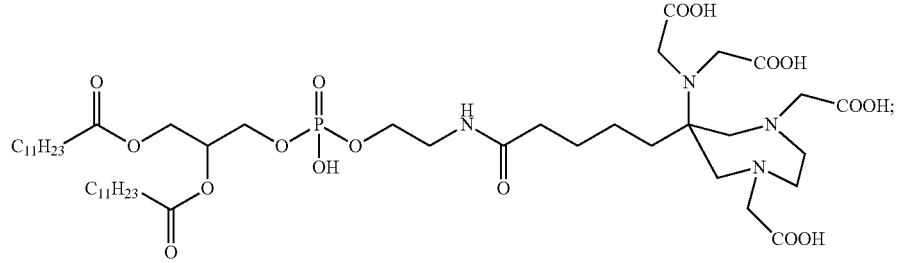
8c
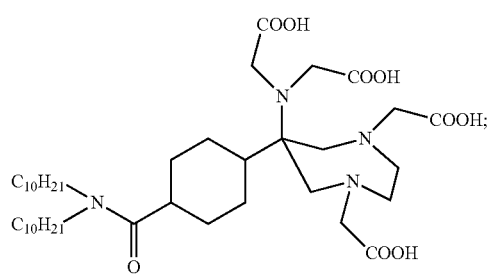
24a
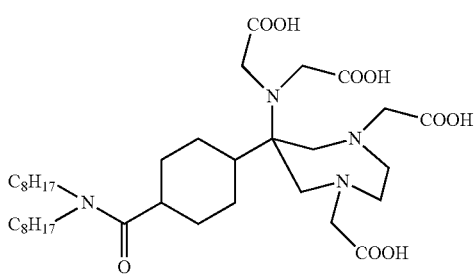
24b -continued

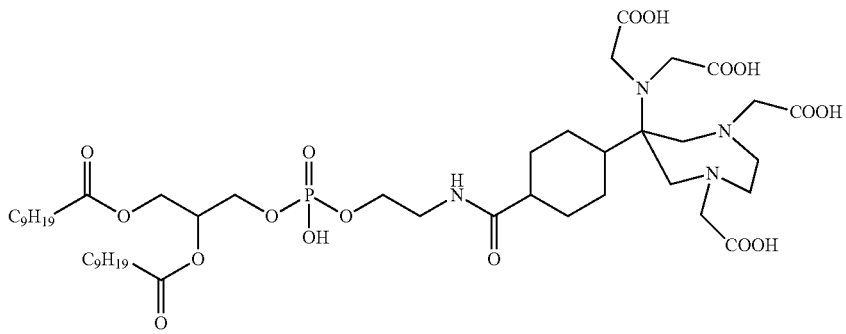

24c or pharmaceutically acceptable salts thereof.

All the above formulae refer to the compounds in an optical pure form as well as component of a racemic mixture thereof.

In another aspect, the invention relates to the compounds of the formula (I) or a pharmaceutical salt thereof as extensively herein described, in the form of a complex with a paramagnetic metal ion, preferably selected from: Gd(III), Mn(II), Cr(III), Cu(II), Fe(III), Pr(III), Nd(III), Sm(III), Tb(III), Yb(III), Dy(III), Ho(III) and Er(III), whereas Gd(III) and Dy(III) are particularly preferred. Of note, such paramagnetic amphiphilic complexes can be prepared by analogy with other known procedures used in the art for the preparation of paramagnetic metal complexes, such as reaction of the precursor derivative of formula (I) with the metal of choice, the latter e.g. in the form of oxide, chloride or acetate, in a suitable solvent, typically water (for a general reference see WO00/30688) or even in organic solvent/water mixtures, typically depending on the source of metal ion employed.

Even further, compound of formula (I), also when in the form of amphiphilic complex as above explained, are generally in the form of a salt with physiologically acceptable bases or physiologically acceptable ions of organic or inorganic acids. In this respect, preferred bases are selected from: primary, secondary, tertiary amines, basic amino acids and inorganic hydroxides of sodium, potassium, magnesium, calcium or mixture thereof. Preferred anions of organic acid are: acetate, succinate, citrate, fumarate, maleate, oxalate; whereas preferred anions of inorganic acids are selected from: hydrogen halides, sulphates, phosphates, phosphonate and the like. Suitable salts can also be formed with cations or anions of amino acids selected from: lysine, arginine, ornithine, aspartic or glutamic acid, and the like.

Preferred compounds of formula (I) in the form of paramagnetic amphiphilic complexes or salts thereof, according to the present invention are selected from:

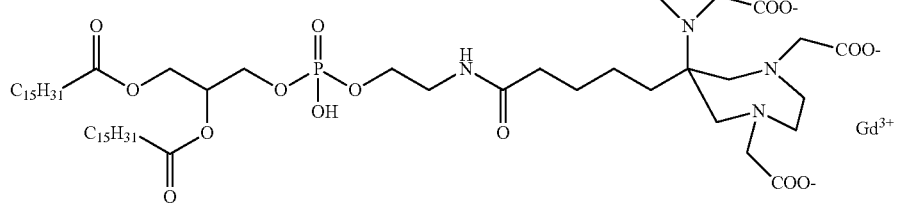

9c

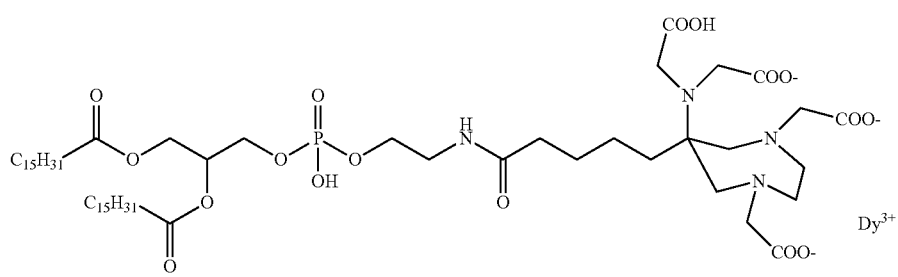

9'c

-continued
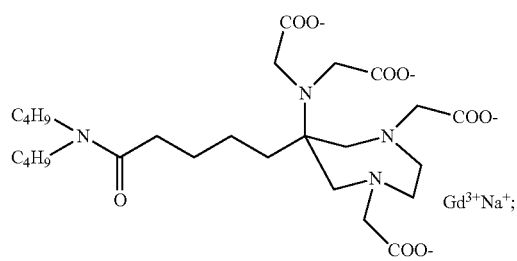
12a
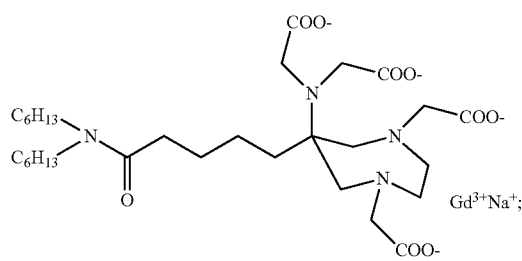
12b
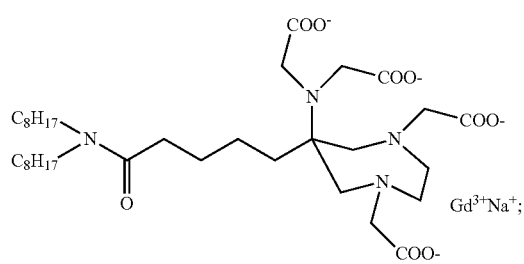
12c
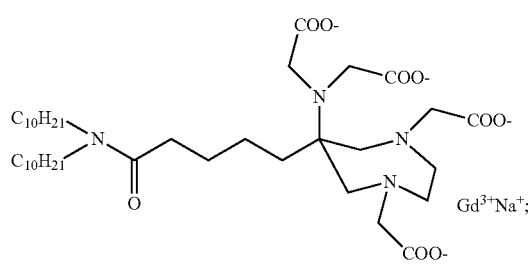
12d
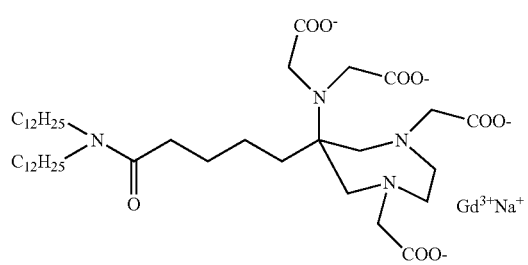
12e
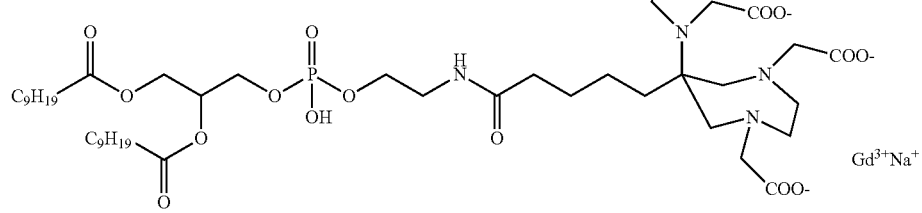
9a
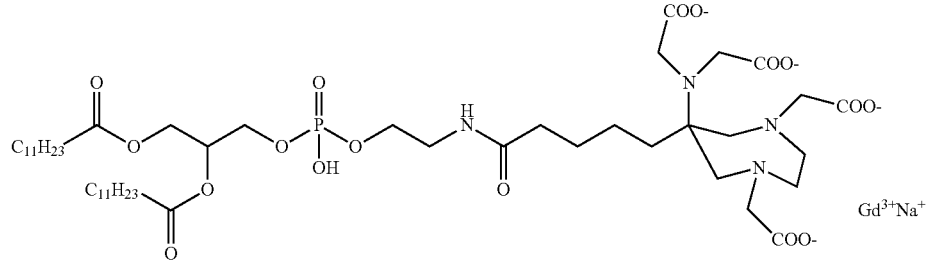
9b
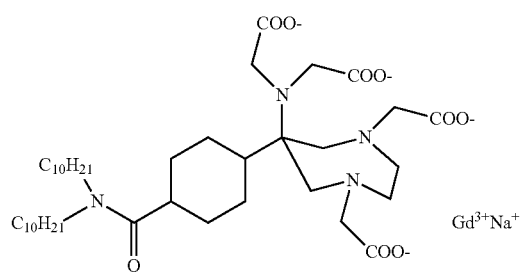
25a
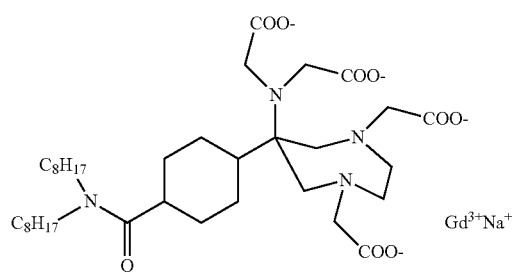
25b

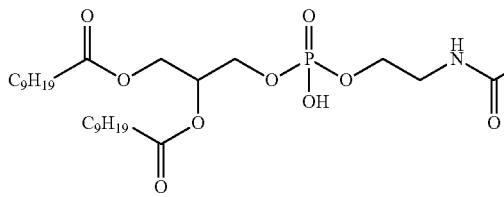
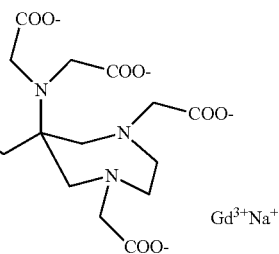

25c

The present paramagnetic complexes or pharmaceutically acceptable salts thereof are suitable for the use as MRI contrast agent. Their use as diagnostic agents in suitable pharmaceutical formulations, is therefore comprised within the scope of the present invention.

The paramagnetic metal complexes according to the present invention show, advantageously, remarkably high relaxivity values, in particular when compared to known contrast agent commercially available and employed in diagnostic experiments. As shown in Table 1 in the experimental part, the relaxivity of the compounds of the invention is unexpectedly high when compared to some other well known compounds used as contrast agent in MRI, such as e.g. gadolinium-tetraazacyclododecanetetraacetic acid (Gd-DOTA). Of note, the amphiphilic complexes of the invention dissolve in aqueous solution and in human plasma and should be taken up more easily by the cell than conventional gadolinium chelates, which are highly hydrophilic.

Therefore, in a further embodiment, the invention relates to the use of an amphiphilic compound of formula (I) in the form of paramagnetic metal complex, or a pharmaceutical acceptable salt thereof, for the preparation of a MRI contrast agent. Even further, such paramagnetic complexes or pharmaceutically acceptable salt thereof, can be conveniently used in the preparation of MRI contrast agents or formulations, particularly useful as blood pool agent, for the imaging of blood microcirculation in tumour, as contrast agent for angiography, as well as for the imaging of inflamed tissues in general.

According to a further aspect, the present invention refers to pharmaceutical acceptable compositions comprising the derivatives of formula (I) or pharmaceutical salts thereof, in the form of paramagnetic metal complex, in admixture with one or more physiologically acceptable excipients, diluents or solvents. In fact both lipophilic and aqueous diluents and/or solvents are equally suitable for the compounds of the present invention, due to their amphiphilic nature. Pharmaceutical compositions can be suitably prepared for administration by any convenient route, e.g. for oral, parenteral, topical (including ophthalmic and nasal) administration. They can also be formulated for administration by inhalation or insufflation (either through the mouth or nose). However, such compositions are preferably injectable compositions, adapted for use as contrast agent in imaging techniques, in particular for MR imaging techniques, and can conveniently be formulated in aqueous solutions or dispersions at a physiologically acceptable pH, for parenteral use.

According to a further embodiment, the compounds of the present invention are particularly suited for the preparation of macromolecular aggregates such as micelles or liposomes, together with physiologically acceptable additives i.e. selected from surfactants amphipatic compounds and/or stealth compounds, such as PEG.

According to this embodiment, the formulations may comprise one or more derivatives of formula (I) in the form of a paramagnetic complex or a salt thereof, in admixture with one or more surfactant and/or amphipatic compounds.

Micelles may be obtained by known techniques, for instance as described in WO97/00087, usually depending on the lipophilic characteristics of residue Y in formula (I). Typically, such micelles can be prepared in any physiologically acceptable aqueous liquid carrier, such as water or saline, neat or buffered, and depending, e.g., on the selected components, the dispersion can be achieved by gentle stirring or by homogenisation, microfluidification or sonication.

The supramolecular aggregates of the invention can be collected, and even stored, as solids in a dry form, after treatment with known methods, e.g. by lyophilization or the like. The dry form (porous lumps or free flowing powder) is particularly convenient for long-term storage. The formulation can then be reconstituted before usage by dispersion of the lyophilized in a physiologically acceptable liquid carrier, thus obtaining a suspension corresponding to the early formulation and directly usable as MRI contrast agent.

In a further aspect of this embodiment, the invention relates to a kit of parts comprising the above described lyophilized components and, separately, the liquid carrier. In particular, the lyophilized components may be stored under a dry, inert atmosphere whereas the carrier liquid may further contain isotonic additives and other physiologically acceptable components, such as amino acids or the like.

According to a further aspect, the invention comprise the process for the preparation of compounds of formula (I) by a process comprising at first the formation an adduct between the selected linker L and the diazepine moiety, followed by activation of the carboxylic function on the terminal side of the linker, followed by amidation with the selected Y group.

The protecting groups, where present are eventually removed by standard techniques and the derivative is preferably optionally complexed with the selected paramagnetic metal.

The adduct between the linker L and the diazepine moiety as starting material of the present process is obtained by reaction of a suitable nitro derivative, which is a precursor of the selected linker moiety, with N,N'-dibenzylethylenediamine, which is the precursor of the diazepine core of the present derivatives, followed by reduction and functionalization of the nitro group, typically by hydrogenation and subsequent N-alkylation under basic conditions. As clearly supported and illustrated in the present experimental part, said adduct between the linker and the diazepine moiety can advantageously be prepared and used as building block for the preparation of a series of derivatives of formula (I) by varying the selected moiety Y. Therefore, it is an aspect of the invention a process for the preparation of the above defined compounds of formula (I):

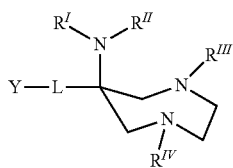

(I)

comprising the steps of:

a) preparation of an adduct of formula:

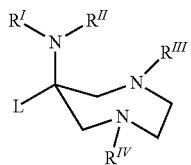

wherein $R^{I-IV}$ are as above defined and L is the linker comprising a terminal carboxylic function, b) activation of said terminal carboxylic function of the linker, c) amidation reaction between the product of step b) and the Y group as above defined;

d) cleavage of any protecting group to give the derivative of formula (I); and optionally e) chelation with a paramagnetic metal ion, to give the derivative of formula (I) in the form of a paramagnetic complex.

According to an illustrative example, the process of the invention can be generally represented by the processes for the preparation of derivative 12a, wherein the compound 5 is the starting adduct, as indicated in the Scheme 1 below:

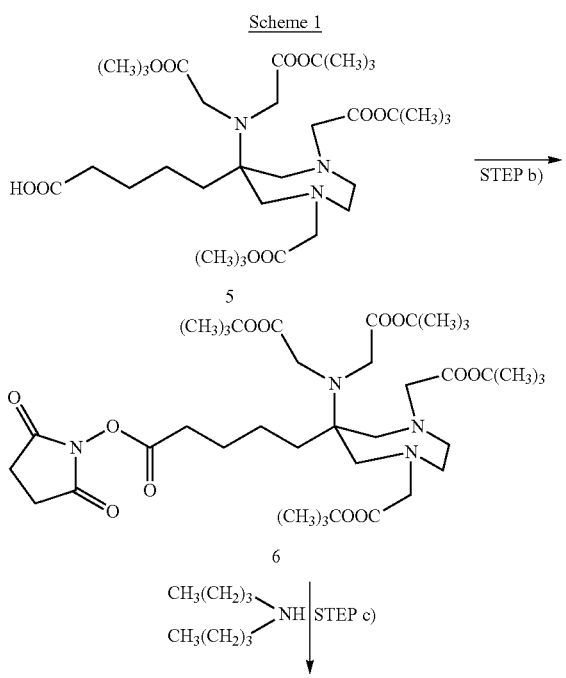

In particular, the adduct 5 between the linker and the diazepine moiety is prepared by reaction of N,N'-dibenzyethylenediamine diacetate and an alcoholic solution of 6-nitrohexanoic acid methyl ester 1, in the presence of paraformaldehyde followed by: reduction and debenzylation of the nitro group 2, functionalization of the amine nitrogen atom 3 and selective cleavage of the terminal carboxylic group 4, as indicated in Scheme 2, herein below:

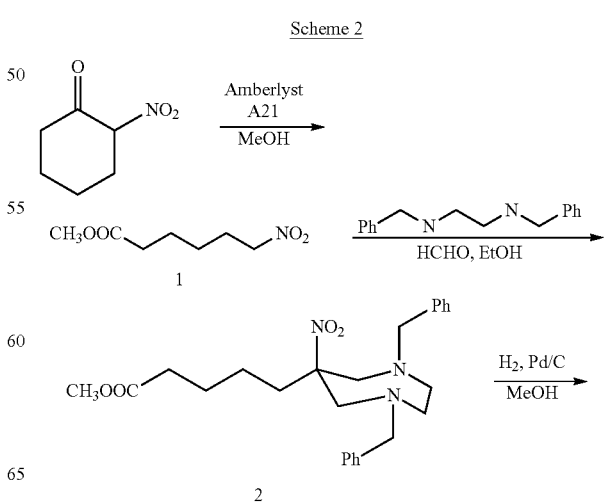

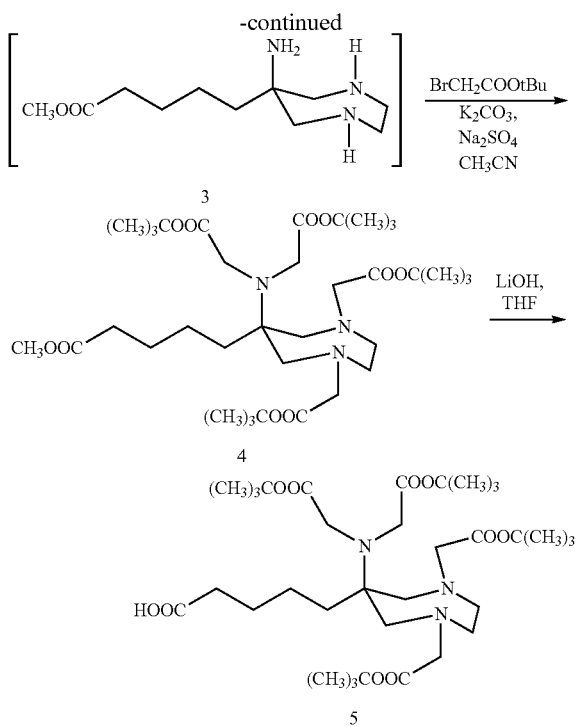

The diazepine adduct, as generally represented by 5, is subjected to the activation of the terminal carboxylic function as per step b) of the present process. In this direction, step b) can be carried out e.g. according to procedures generally known in organic chemistry for the activation of carboxylic functions, typically by reaction with a carboxyl activating agent, such as N-hydroxysuccinimide (NHS) in the presence of a carbodiimide such as dicyclohexylcarbodiimide (DCC) or 1-ethyl-3-(3-dimethylaminopropyl)-carbodiimide (EDC), in a molar ratio of at least 1:1 or preferably in a slight excess with respect to the starting material, e.g. in a molar ratio up to 1:1.5, in a proper organic solvent, such as an apolar organic solvent selected from: $CHCl_3$, $CH_2Cl_2$ and the like. Preferably, step b) is conducted in the presence of N-hydroxysuccinimide (NHS) and EDC in a molar ratio from 1:1 to 1:1.1 with respect to the starting material, and in the presence of $CH_2Cl_2$. The thus obtained derivative is then subjected according to step c) to an amidation reaction between the thus activated carboxylic terminal group of the linker L and the nitrogen atom of the selected Y residue for instance dibutylamine, generally in the presence of a diisopropylethylamine (DIPEA). Preferably, the amidation reaction is carried out by dissolving the activated compound obtained after step b) in $CHCl_3$ and adding for instance dibutylamine and DIPEA in this order in a molar ratio from 1:1 to 1:1.7 with respect to the activated starting material. The solution is then stirred for a proper frame of time at a selected temperature, typically at room temperature (e.g. at a temperature comprised from 15 to 30° C.) generally for a period up to 20-24 hours. The thus formed amide product can be conveniently worked up, e.g. by washing with water and by evaporating the separated organic phase, generally under vacuum or distillation procedure. After purification, for instance by chromatography, the product of formula (I) is obtained in a protected form, e.g. preferably as tert-butyl ester derivative, in high yield (about 80%) and with a high degree of purity (about 95-99% HPLC).

According to step d) the derivatives of formula (I) obtained in their carboxylic protected form, can be readily deprotected under conditions known in the art, and dependent for instance on the kind of protecting group actually employed in step a). For a general reference on the choice of possible protecting groups, see "Greene's protective groups in organic synthesis" Wiley 14th Ed.

In a preferred embodiment, the carboxylic function is protected as tert-butyl ester, and the deprotection is carried out under acidic conditions, typically in the presence of trifluoroacetic acid (TFA) and an organic apolar solvent such as $CH_2Cl_2$.

After deprotection, the thus obtained compounds of formula (I) can suitably be reacted with a metal ion containing compound in order to obtain the corresponding metal complex derivatives. Said transformation is typically carried out by reaction with an inorganic or organic salt or oxide of the selected metal, operating in the presence of a solvent such as water or organic solvent, e.g. $CHCl_3$ or MeOH, or mixture thereof. Preferred counter ions are chloride or acetate, and preferred salts are: $GdCl_3$, $DyCl_3$, $Gd(OAc)_3$ or $Dy(OAc)_3$, whereas preferred oxides are: $Gd_2O_3$ or $Dy_2O_3$.

As formerly reported, the derivatives of formula (I) of the present invention, in the form of a paramagnetic complex, are endowed with a particularly high degree of relaxivity (generally indicated as rip) and long lasting activity and stability, as demonstrated in the present Experimental part, Table I and Table II. Relaxivity ($r_{1p}$) is an intrinsic property of paramagnetic complexes which characterizes their ability to increase the nuclear magnetic relaxation rate of vicinal protons. High relaxation rates, i.e. high relaxivity values, ensure increased contrast in the image, which makes possible to obtain diagnostic information in a short time frame. On the other hand, a long lasting activity and stability ensure both a visualization of the contrast agent for a proper frame of time, thus allowing a better and clear identifications of the regions analysed during the imaging method, and a proper excretion time from the body, thus avoiding unnecessary retaining of the contrast media within the sample.

Therefore, the present derivatives are particularly suitable for the use in the preparation of a diagnostic composition to be used in MRI techniques. Hence, according to another aspect, the present invention provides a method for imaging of body regions comprising administering to a subject to be imaged a diagnostically effective amount of a composition of the invention. Preferably said method is a MRI method comprising administering to a subject to be imaged a diagnostically effective amount of a composition of the invention comprising a compound of formula (I) in the form of complex with a paramagnetic metal ion, wherein said metal ion is preferably selected from $Gd^{3+}$ and $Dy^{3+}$.

The present invention thus refers to a method for operating an imaging system, comprising the steps of:
  a) submitting a subject pre-administered with a composition of the invention and positioned in said imaging system, to a radiation frequency selected to interact with the active substrate of said composition; and
  b) recording a signal from said interaction.

Even more preferably, the invention refers to a MRI method comprising the steps of:
  a) submitting a subject pre-administered with a composition of the invention comprising a compound of formula (I) in the form of a paramagnetic complex, to a radiation frequency selected to excite nuclear spin transitions in a non-zero nuclear spin nuclei of said active substrate; and
  b) recording a MR signal from said excited nuclei.

As extensively reported above, the present invention advantageously provides a new class of diazepine of formula (I) and pharmaceutical salts thereof, obtainable by a straight full and convenient process, useful for the preparation of paramagnetic complexes, employable e.g. as contrast agent in MRI analysis. Even further, the relaxivity ($r_{1p}$) values of the present paramagnetic complexes are surprisingly high, thus rendering them a valid and convenient alternative to the prior art complexes as MRI contrast agents. Advantageously, the present complexes can be administered as pharmaceutical compositions, showing a high relaxation rate and stability, thus allowing a low dosage.

The following examples are only representative of the invention and are not intended to limit its scope.

EXPERIMENTAL PART

Example 1

Preparation of Compounds 9(a-c)

General Synthetic Scheme 3:

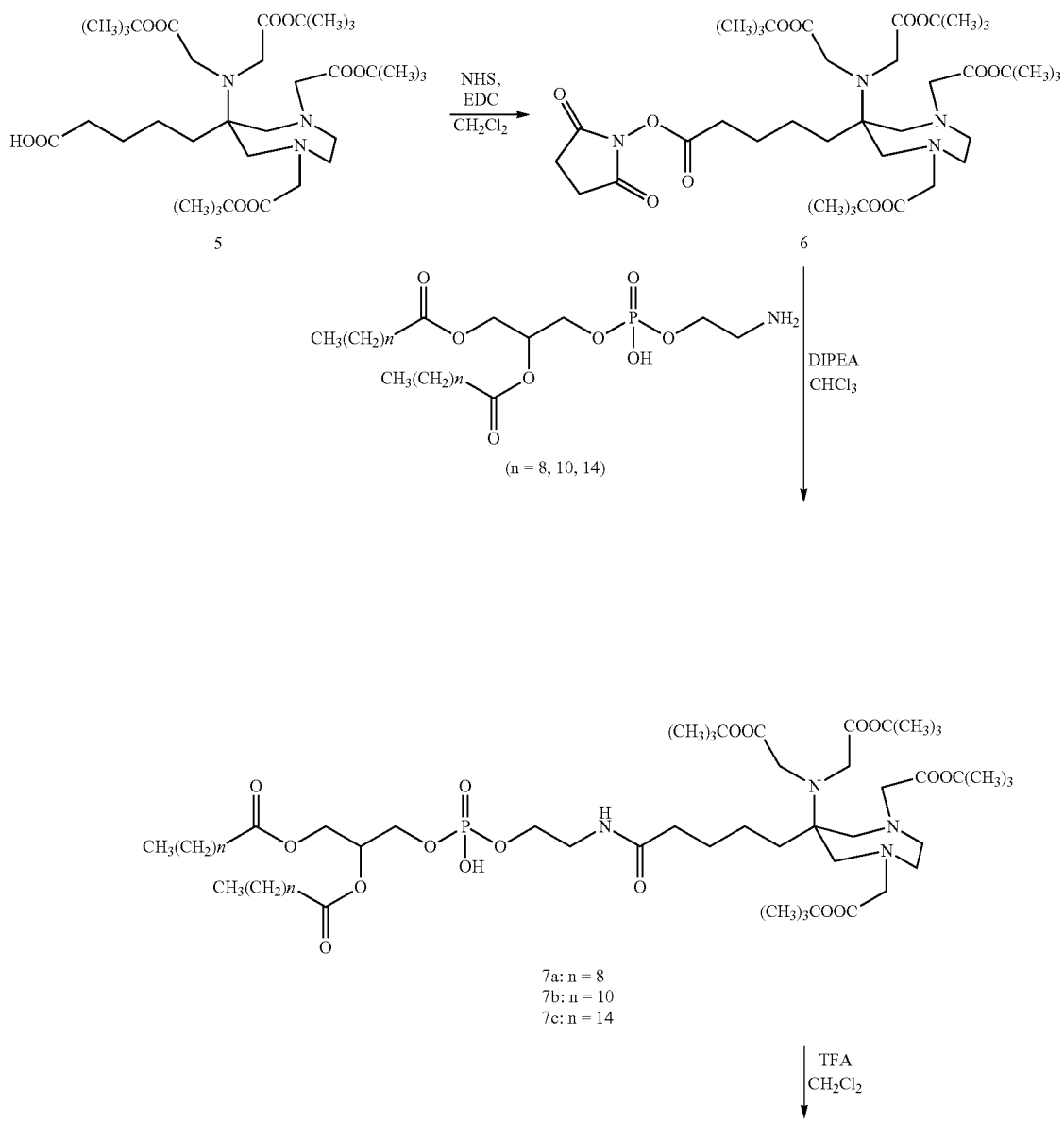

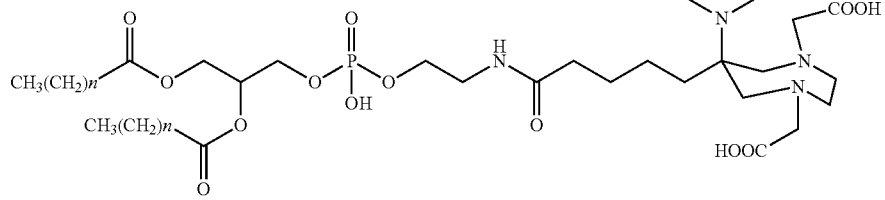

8a: n = 8
8b: n = 10
8c: n = 14

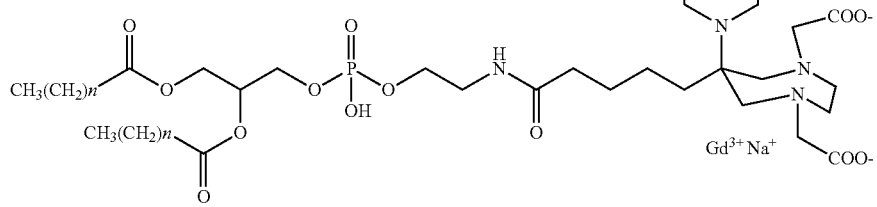

9a: n = 8
9b: n = 10
9c: n = 14

Example 1.1 Preparation of Compound 5

Compound 5 was prepared in five steps according to the procedure described in US2006018830 as illustrated in the Scheme 2 below.

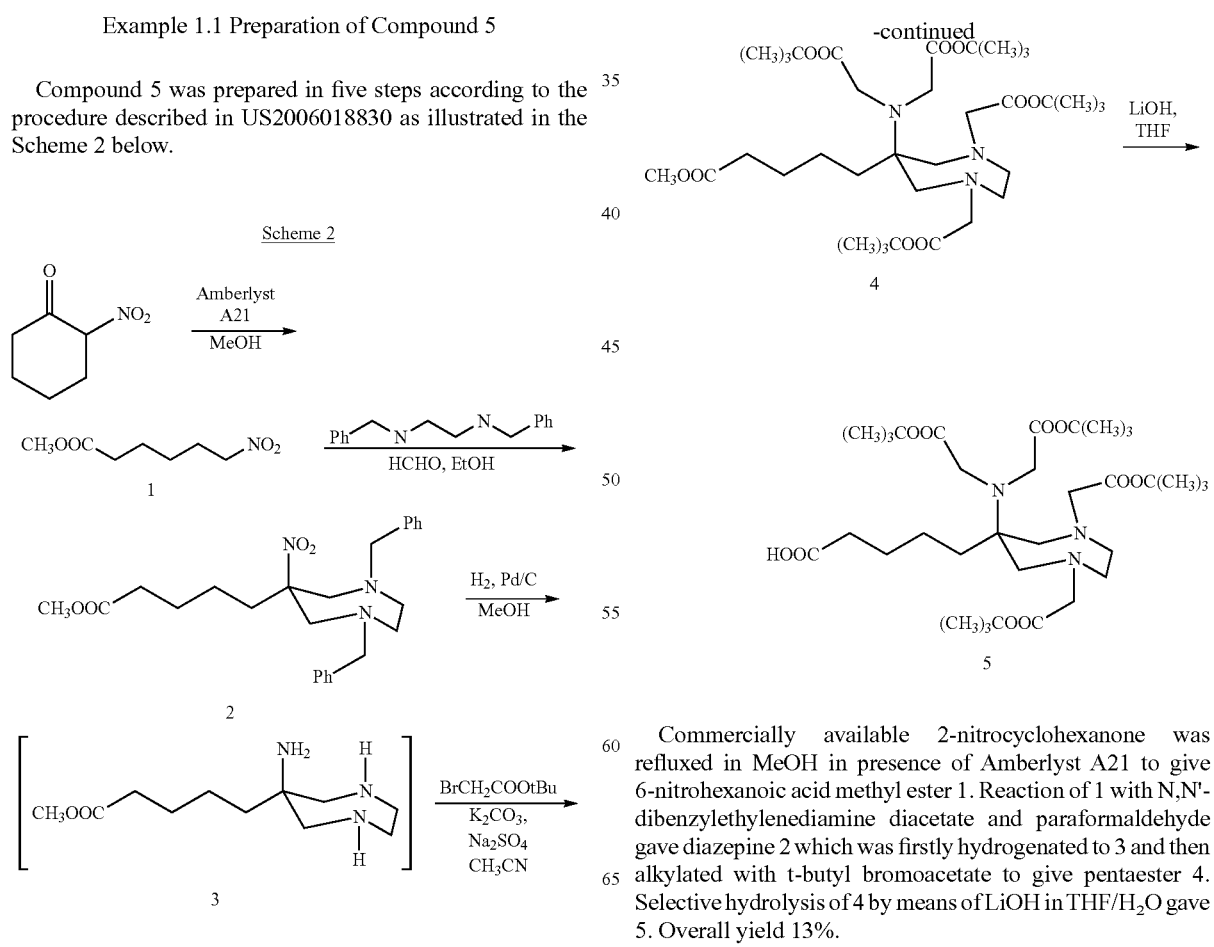

Commercially available 2-nitrocyclohexanone was refluxed in MeOH in presence of Amberlyst A21 to give 6-nitrohexanoic acid methyl ester 1. Reaction of 1 with N,N'-dibenzylethylenediamine diacetate and paraformaldehyde gave diazepine 2 which was firstly hydrogenated to 3 and then alkylated with t-butyl bromoacetate to give pentaester 4. Selective hydrolysis of 4 by means of LiOH in THF/H$_2$O gave 5. Overall yield 13%.

Example 1.1a

Preparation of Compound 6

6-[Bis[2-[(1,1-dimethyl)ethoxy]-2-oxoethyl]amino]-6-[(2,5-dioxo-1-pyrrolidinyl)oxy]-5-oxopent-1-yl]-tetrahydro-1H-1,4-diazepine-1,4(5H)-diacetic acid bis[(1,1-dimethyl)ethyl]ester Compound 5 (14.6 g; 0.022 mol) was dissolved in $CH_2Cl_2$ (350 mL), then NHS was added (3.75 g; 0.033 mol) and the mixture was cooled at 0° C. with an ice-bath. A solution of EDC (6.25 g; 0.033 mol) in $CH_2Cl_2$ (150 mL) was added drop wise, then the reaction solution was stirred for 24 h at room temperature. The mixture was washed with $H_2O$ (3×150 mL). The organic phase was dried ($Na_2SO_4$), filtered and evaporated to give 6 as a yellow oil (15.42 g; 0.020 mol).

Yield 92%.
Analytical data:
Mr: 768.94 (C38H64N4O12)
$^1$H- and $^{13}$C-NMR and MS are compatible with the structure

Example 1.2

Preparation of Compounds 7(a-c). General Procedure

Compound 6 (1 eq) was dissolved in $CHCl_3$ (concentration 1% w/v). The suitable phosphoethanolamine (1 eq) (1,2-didecanoyl-sn-glycero-3-phosphoethanolamine, DLPE or DPPE) and diisopropylethylamine (DIPEA) (1.7 eq) were added in this order. The solution was stirred at room temperature from 3 h to 24 h. The mixture was washed subsequently with $H_2O$ (1×50 mL), acidic $H_2O$ (pH 4-5 with HCl; 1×50 mL) and $H_2O$ (1×50 mL). The organic phase was dried ($Na_2SO_4$), filtered and evaporated. The crude thus obtained was purified by flash chromatography to give compounds 7(a-c) as a white solid.

Example 1.2a

Preparation of Compound 7a

6-[Bis[2-[(1,1-dimethyl)ethoxy]-2-oxoethyl]amino]-6-[(13R)-10-hydroxy-10-oxido-5,16-dioxo-13-(1-oxodecyl)oxy]-9,11,15-trioxa-6-aza-10-phosphapentacos-1-yl]-tetrahydro-1H-1,4-diazepine-1,4(5H)-diacetic acid bis[(1,1-dimethyl)ethyl]ester Starting materials: Compound 6 (797 mg; 1.04 mmol); 1,2-didecanoyl-sn-glycero-3-phosphoethanolamine (543 mg; 1.04 mmol)

Compound 7a (937 mg; 0.796 mmol). Yield 77%.
Analytical data:
HPLC-ELSD: ELSD 100% (area %); UV 89.1% (area %)
Mr: 1177.50 (C59H109N4O17P)
$^1$H- and $^{13}$C-NMR and MS are compatible with the structure

Example 1.2b

Preparation of Compound 7b

6-[Bis[2-[(1,1dimethyl)ethoxy]-2-oxoethyl]amino]-6-[(13R)-10-hydroxy-10-oxido-5,16-dioxo-13-(1-oxododecyl)oxy]-9,11,15-trioxa-6-aza-10-phosphaeptacos-1-yl]-tetrahydro-1H-1,4-diazepine-1,4(5H)-diacetic acid bis[(1,1-dimethyl)ethyl]ester Starting materials: Compound 6 (700 mg; 0.91 mmol); 1,2-dilauroyl-sn-glycero-3-phosphoethanolamine DLPE (500 mg; 0.86 mmol)

Compound 7b (927 mg; 0.751 mmol). Yield 87%.
Analytical data:
HPLC-ELSD: ELSD 100% (area %); UV 80.0% (area %)
Mr: 1233.61 (C63H117N4O17P)
$^1$H- and $^{13}$C-NMR and MS are compatible with the structure

Example 1.2c

Preparation of Compound 7c

6-[Bis[2-[(1,1dimethyl)ethoxy]-2-oxoethyl]amino]-6-[(13R)-10-hydroxy-10-oxido-5,16-dioxo-13-(1-oxoesadecyl)oxy]-9,11,15-trioxa-6-aza-10-phosphanonacos-1-yl]-tetrahydro-1H-1,4-diazepine-1,4(5H)-diacetic acid bis[(1,1-dimethyl)ethyl]ester Starting materials: Compound 6 (1.92 g; 2.50 mmol); 1,2-dipalmitoyl-sn-glycero-3-phosphoethanolamine DPPE (1.73 g; 2.50 mmol).

Compound 7c (2.79 g; 2.07 mmol). Yield 83%.
Analytical data:
HPLC-ELSD: ELSD 100% (area %); UV 89.0% (area %)
Mr: 1345.82 (C71H133N4O17P)
$^1$H- and $^{13}$C-NMR and MS are compatible with the structure

Example 1.3

Cleavage of t-Butyl Esters. General Procedure

Compound 7(a-c) (1 eq) was dissolved in $CH_2Cl_2$ (concentration 2-4% w/v) and the solution was stirred and cooled at 0° C., then TFA (6 eq) was added drop wise. The reaction mixture was stirred for 1 h at room temperature. The orange solution was evaporated and the residue was dissolved in fresh TFA (30 eq) was added. This solution was stirred for 80 h at room temperature; the reaction was monitored by MS and HPLC-ELSD. The mixture was evaporated and the residue was treated with diisopropyl ether to obtain a white solid that was centrifuged and washed with diisopropyl ether (2×30 mL). That solid was suspended in $H_2O$, dissolved at pH 6-7 by addition of 5% aq $NaHCO_3$ and precipitated at pH 2 by addition of 1M HCl. The solid was filtered and dried at reduced pressure ($P_2O_5$) to obtain the ligands 8(a-c) according to the data below.

Example 1.3a

Preparation of Compound 8a

6-[Bis[2-[(carboxy)methyl]amino]-6-[(13R)-10-hydroxy-10-oxido-5,16-dioxo-13-(1-oxodecyl)oxy]-9,11,15-trioxa-6-aza-10-phosphapentacos-1-yl]-tetrahydro-1H-1,4-diazepine-1,4(5H)-diacetic acid Starting material: Compound 7a (885 mg; 0.752 mmol).
Compound 8a (669 mg; 0.702 mmol); Yield 93%
Analytical data:
HPLC-ELSD: ELSD 92.3% (area %)
Mr: 953.07 ($C_{43}H_{77}N_4O_{17}P$)
Complexometric Titer (1.001 mM $GdCl_3$): 95.7%
$^1H$- and $^{13}C$-NMR and MS are compatible with the structure

Example 1.3b

Preparation of Compound 8b

6-[Bis[2-[(carboxy)methyl]amino]-6-[(13R)-10-hydroxy-10-oxido-5,16-dioxo-13-(1-oxododecyl)oxy]-9,11,15-trioxa-6-aza-10-phosphaeptacos-1-yl]-tetrahydro-1H-1,4-diazepine-1,4(5H)-diacetic acid Starting material: Compound 7b (875 mg; 0.709 mmol).
Compound 8b (750 mg; 0.642 mmol); Yield 91%
Analytical data:
HPLC-ELSD: ELSD 75.5% (area %)
Mr: 1009.18 ($C_{47}H_{85}N_4O_{17}P$)
$^1H$- and $^{13}C$-NMR and MS are compatible with the structure

Example 1.3c

Preparation of Compound 8c

6-[Bis[2-[(carboxy)methyl]amino]-6-[(13R)-10-hydroxy-10-oxido-5,16-dioxo-13-(1-oxoesadecyl)oxy]-9,11,15-trioxa-6-aza-10-phosphanonacos-1-yl]-tetrahydro-1H-1,4-diazepine-1,4(5H)-diacetic acid Starting material: Compound 7c (2.79 g; 2.07 mmol)
Compound 8c (1.77 g; 1.58 mmol); Yield 76% Analytical data:
HPLC-ELSD: ELSD 95.3% (area %)
Mr: 1121.39 ($C_{55}H_{101}N_4O_{17}P$)
Complexometric Titer (1.001 mM $GdCl_3$): 95.7%
$^1H$- and $^{13}C$-NMR and MS are compatible with the structure

Example 1.4

Complexation in Aqueous Media. General Procedure

The ligands 8(a-c) (1 eq) was suspended in $H_2O$ (concentration 5%; starting pH 1-2) and dissolved at pH 6.5-7 by addition of 5% aq $NaHCO_3$. A titrated solution of $GdCl_3$ (1 eq) was added in portions. The solution was stirred at room temperature and pH was maintained by addition of 5% aq $NaHCO_3$. The complexation was monitored by HPLC-ELSD and with Xylenol Orange assay. The crude complexes were isolated by lyophilization and were purified from salts by size exclusion chromatography to give 9(a-c).

Example 1.4a

Preparation of Compound 9a

[[6-[Bis[2-[(carboxy)methyl]amino]-6-[(13R)-10-hydroxy-10-oxido-5,16-dioxo-13-(1-oxodecyl)oxy]-9,11,15-trioxa-6-aza-10-phosphapentacos-1-yl]-tetrahydro-1H-1,4-diazepine-1,4(5H)-diacetate(4-)]gadolinate(1-)]sodium Starting material: Compound 8a (400 mg; 0.438 mmol)
Compound 9a (257 mg; 0.228 mmol); Yield 52%
Analytical data:
HPLC-ELSD: ELSD 98.9% (area %)
Mr: 1129.28 ($C_{43}H_{73}GdN_4NaO_{17}P$)
MS is compatible with the structure

Example 1.4b

Preparation of Compound 9b

[6-[Bis[2-[(carboxy)methyl]amino]-6-[(13R)-10-hydroxy-10-oxido-5,16-dioxo-13-(1-oxododecyl)oxy]-9,11,15-trioxa-6-aza-10-phosphaeptacos-1-yl]-tetrahydro-1H-1,4-diazepine-1,4(5H)-diacetate(4-)]gadolinate(1-)]sodium Starting material: Compound 8b (690 mg; 0.590 mmol)
Compound 9b (614 mg; 0.518 mmol); Yield 88%
Analytical data:
HPLC-ELSD: ELSD 95.6% (area %)
Mr: 1185.39 ($C_{47}H_{81}GdN_4NaO_{17}P$)
MS is compatible with the structure

Example 1.4c

Preparation of Compound 9c

[6-[Bis[2-[(carboxy)methyl]amino]-6-[(13R)-10-hydroxy-10-oxido-5,16-dioxo-13-(1-oxoesadecyl)oxy]-9,11,15-trioxa-6-aza-10-phosphanonacos-1-yl]-tetrahydro-1H-1,4-diazepine-1,4(5H)-diacetate(4-)]gadolinate(1-)]sodium Starting material: Compound 8c (500 mg; 0.435 mmol)
Compound 9c (517 mg; 0.398 mmol); Yield: 92%
Analytical data:
HPLC-ELSD: ELSD 99.2% (area %) [8]
Mr: 1297.60 ($C_{55}H_{97}GdN_4NaO_{17}P$)
MS is compatible with the structure

Example 1.5

Complexation in Organic Media. Preparation of Compound 9b

[6-[Bis[2-[(carboxy)methyl]amino]-6-[(13R)-10-hydroxy-10-oxido-5,16-dioxo-13-(1-oxododecyl)oxy]-9,11,15-trioxa-6-aza-10-phosphaeptacos-1-yl]-tetrahydro-1H-1,4-diazepine-1,4(5H)-diacetate(4-)]gadolinate(1-)]sodium 9b The ligand 8b was complexed alternatively in organic media. Ligand 8b (0.506 g; 0.475 mmol) was dissolved in CHCl₃ (70 mL) and a solution of Gd(OAc)₃ 0.011 M in 10:1 v/v MeOH/H₂O (29.1 mL; 0.309 mmol) was added in portions. Subsequently, the pH was adjusted to 7 using pyridine. The complexation was monitored by HPLC-ELSD and with Xylenol Orange assay and finally the solution was evaporated under reduced pressure. The residue was dissolved subsequently in 1:1 v/v MeOH/toluene (3×30 mL) and CHCl₃ (3×30 mL) and evaporated after each dissolution then the oily residue was suspended in H₂O and lyophilized. The white solid was suspended in H₂O, adjusted to pH 7 and lyophilized; the latter treatment was repeated twice to obtain Compound 9b as a white solid (0.750 g).

Quantitative yield.
Analytical data: HPLC-ELSD: ELSD 82.6% (area %)
Mr: 1185.39 (C47H81GdN4NaO17P).
MS is compatible with the structure

Example 2

Preparation of Compounds 12(a-e)

Compounds 12(a-e) are prepared according to the Scheme 4:

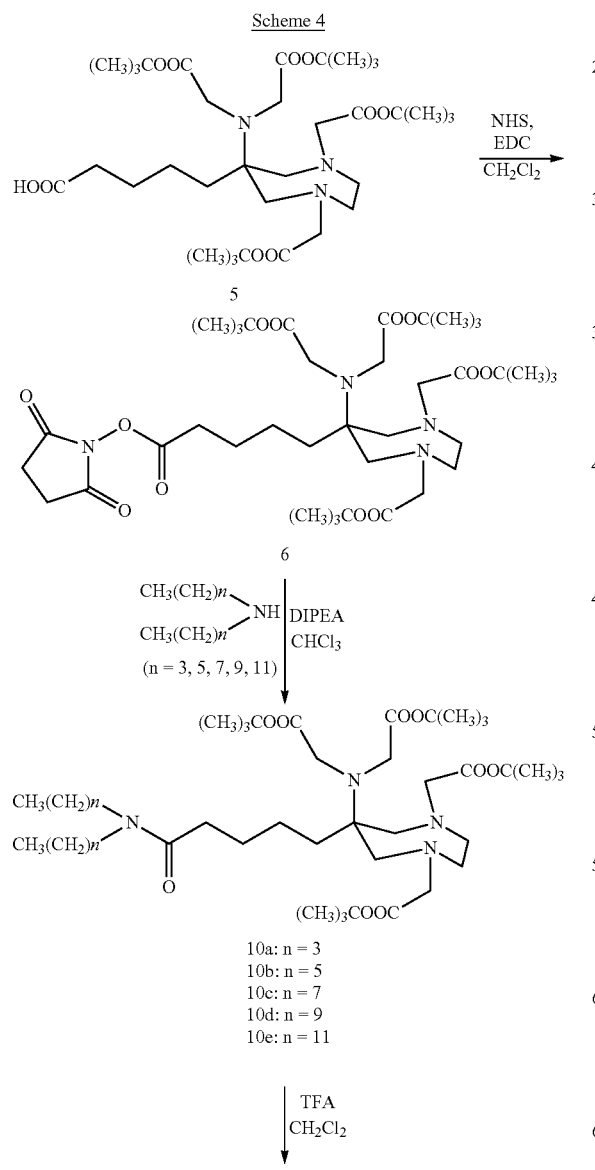
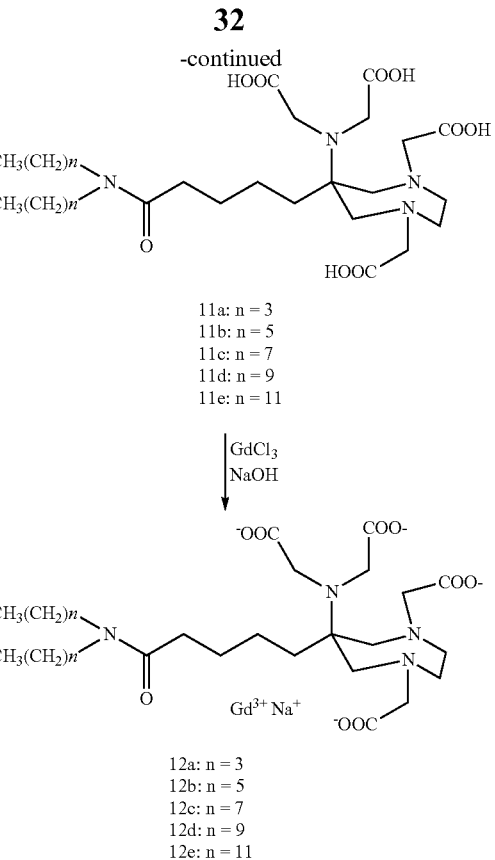

Example 2.1

Preparation of Compounds 10(a-e). General Procedure

Compound 6 prepared according to Example 1.1a (1 eq) was dissolved in CHCl₃ (concentration 1-3% w/v) then the suitable dialkylamine (1 eq) and DIPEA (1.7 eq) were added subsequently. The reaction solution was stirred at room temperature for 24 h then was washed subsequently with H₂O (1×50 mL), acidic H₂O (pH 4-5 with HCl; 1×70 mL) and H₂O (1×50 mL). The organic phase was dried (Na₂SO₄), filtered and evaporated. The crude thus obtained was purified by flash chromatography to give compounds 10(a-e) as an oil, according to the results as indicated below:

Example 2.1a

Preparation of Compound 10a

6-[Bis[2-[(1,1-dimethyl)ethoxy]-2-oxoethyl]amino]-6-[5-(dibutylamino)-5-oxopent-1-yl]-tetrahydro-1H-1,4-diazepine-1,4(5H)-diacetic acid bis[(1,1-dimethylethyl)]ester Starting materials: Compound 6 (1.50 g; 1.95 mmol); dibutylamine (0.332 mL; 1.95 mmol)

Compound 10a (1.51 g; 1.93 mmol). Yield 98% Analytical data:

HPLC-ELSD: ELSD 95.8% (area %); UV 92.0% (area %)
Mr: 783.10 (C42H78N4O9)
¹H- and ¹³C-NMR and MS are compatible with the structure

Example 2.1b

Preparation of Compound 10b

6-[Bis[2-[(1,1-dimethyl)ethoxy]-2-oxoethyl]amino]-6-[5-(dihexylamino)-5-oxopent-1-yl]-tetrahydro-1H-1,4-diazepine-1,4(5H)-diacetic acid-bis[(1,1-dimethylethyl)]ester Starting materials: Compound 6 (2.50 g; 3.25 mmol); dihexylamine (0.758 mL; 3.25 mmol)
Compound 10b (1.70 g; 2.03 mmol). Yield: 62%.
Analytical data:
HPLC-ELSD: ELSD 99.0% (area %); UV 99.5% (area %)
Mr: 839.21 ($C_{46}H_{86}N_4O_9$).
$^1$H- and $^{13}$C-NMR and MS are compatible with the structure

Example 2.1c

Preparation of Compound 10c

6-[Bis[2-[(1,1-dimethyl)ethoxy]-2-oxoethyl]amino]-6-[5-(dioctylamino)-5-oxopent-1-yl]-tetrahydro-1H-1,4-diazepine-1,4(5H)-diacetic acid-bis[(1,1-dimethylethyl)]ester Starting materials: Compound 6 (2.50 g; 3.25 mmol); dioctylamine (0.981 mL; 3.25 mmol)
Compound 10c (2.16 g; 2.41 mmol). Yield: 74%.
Analytical data:
HPLC-ELSD: ELSD 98.7% (area %); UV 99.3% (area %)
Mr: 895.31 ($C_{50}H_{94}N_4O_9$)
$^1$H- and $^{13}$C-NMR and MS are compatible with the structure

Example 2.1d

Preparation of Compound 10d

6-[Bis[2-[(1,1-dimethyl)ethoxy]-2-oxoethyl]amino]-6-[5-(didecylamino)-5-oxopent-1-yl]-tetrahydro-1H-1,4-diazepine-1,4(5H)-diacetic acid bis[(1,1-dimethylethyl)]ester Starting materials: Compound 6 (1.92 g; 2.50 mmol); didecylamine (0.743 g; 2.50 mmol)
Compound 10d (2.26 g; 2.38 mmol). Yield: 95%.
Analytical data:
HPLC-ELSD: ELSD 95.3% (area %); UV 87.7% (area %)
Mr: 951.42 ($C_{54}H_{102}N_4O_9$)
$^1$H- and $^{13}$C-NMR and MS are compatible with the structure

Example 2.1e

Preparation of Compound 10e

6-[Bis[2-[(1,1-dimethyl)ethoxy]-2-oxoethyl]amino]-6-[5-(didodecylamino)-5-oxopent-1-yl]-tetrahydro-1H-1,4-diazepine-1,4(5H)-diacetic acid-bis[(1,1-dimethylethyl)]ester Starting materials: Compound 6 (3.13 g; 4.07 mmol); didodecylamine (1.44 g; 4.07 mmol)
Compound 10e (4.30 g; 4.27 mmol). Yield: 105% (solvent residue).
Analytical data:
HPLC-ELSD: ELSD 89.7% (area %); UV 93.0% (area %)
Mr: 1007.53 ($C_{58}H_{110}N_4O_9$).
$^1$H- and $^{13}$C-NMR and MS are compatible with the structure

Example 2.2

Preparation of Compounds 11(a-e). General Procedure

Compound 10(a-e) (1 eq) was dissolved in $CH_2Cl_2$ (20-50 mL) and the solution obtained was stirred and cooled at 0° C., then TFA (6 eq) was added drop wise. The reaction mixture was stirred for 1 h at room temperature. The orange solution was evaporated and the residue was dissolved in fresh TFA (50 eq). This solution was stirred for 80 h; the reaction was monitored by MS and HPLC-ELSD. The mixture was evaporated and the residue was treated with diisopropyl ether (70 mL) to obtain a white precipitate that was filtered or centrifuged, washed with diisopropyl ether (2×20 mL) and dried at reduced pressure ($P_2O_5$; NaOH pellets). This procedure was applied to obtain ligands 11a, 11b and 11c as solid. Conversely for 11d and 11e, after the ether treatment, the crude ether was suspended in $H_2O$, dissolved at pH 6-7 by addition of 2N NaOH and precipitated at pH 2 by addition of 1M HCl. The solid was filtered and dried at reduced pressure ($P_2O_5$) to obtain ligands 11d and 11e as white solids.

Example 2.2a

Preparation of Compound 11a

6-[Bis[(carboxy)methyl]amino]-6-[5-(dibutylamino)-5-oxopent-1-yl]-tetrahydro-1H-1,4-diazepine-1,4(5H)-diacetic acid Starting material: Compound 10a (1.40 g; 1.79 mmol)
Compound 11a: (0.868 g; 1.55 mmol); Yield: 86%
Analytical data:
HPLC-ELSD: ELSD 93.0% (area %)
Mr: 558.67 ($C_{26}H_{46}N_4O_9$)
$^1$H- and $^{13}$C-NMR and MS are compatible with the structure

Example 2.2b

Preparation of Compound 11b

6-[Bis[(carboxy)methyl]amino]-6-[5-(dihexylamino)-5-oxopent-1-yl]-tetrahydro-1H-1,4-diazepine-1,4(5H)-diacetic acid Starting material: Compound 10b (1.70 g; 2.03 mmol)
Compound 11b: (1.28 g; 2.08 mmol); Quantitative yield
Analytical data:
HPLC-ELSD: ELSD 57.7% (area %)
Mr: 614.78 ($C_{30}H_{54}N_4O_9$)

Example 2.2c

Preparation of Compound 11c

6-[Bis[(carboxy)methyl]amino]-6-[5-(dioctylamino)-5-oxopent-1-yl]-tetrahydro-1H-1,4-diazepine-1,4(5H)-diacetic acid Starting material: Compound 10c (2.16 g; 2.41 mmol)
Compound 11c (1.31 g; 1.95 mmol); Yield: 81%
Analytical data:
HPLC-ELSD: ELSD 78.6% (area %)
Mr: 670.45 (C34H62N4O9)
Complexometric Titer (0.963 mM $GdCl_3$): 95%
$^1H$- and $^{13}C$-NMR and MS are compatible with the structure

Example 2.2d

Preparation of Compound 11d

6-[Bis[(carboxy)methyl]amino]-6-[5-(didecylamino)-5-oxopent-1-yl]-tetrahydro-1H-1,4-diazepine-1,4(5H)-diacetic acid Starting material: Compound 10d (2.20 g; 2.31 mmol)
Compound 11d (1.08 g; 1.48 mmol); Yield: 64%
Analytical data:
HPLC-ELSD: ELSD 95.7% (area %)
Mr: 726.99 (C38H70N4O9)
Complexometric Titer (1.001 mM $GdCl_3$): 94%
$^1H$- and $^{13}C$-NMR and MS are compatible with the structure

Example 2.2e

Preparation of compound 11e

6-[Bis[(carboxy)methyl]amino]-6-[5-(didodecylamino)-5-oxopent-1-yl]-tetrahydro-1H-1,4-diazepine-1,4(5H)-diacetic acid Starting material: Compound 10e (4.30 g; 4.27 mmol);
Compound 11e (2.83 g; 3.61 mmol); Yield: 85%
Analytical data:
HPLC-ELSD: ELSD 82.4% (area %).
Mr: 783.10 (C42H78N4O9).
$^1H$- and $^{13}C$-NMR and MS are compatible with the structure

Example 2.3

Preparation of Compounds 12(a-e). General Procedure

The ligands 11(a-e) (1 eq) were suspended in $H_2O$ (concentration 5% w/v; starting pH 1-2), and dissolved at pH 6.5-7 by addition of 2N NaOH. A titrated solution of $GdCl_3$ (1 eq) was added in portions. The mixture was stirred at room temperature and pH was maintained by addition of 0.1N NaOH. The complexation was monitored by HPLC-ELSD and with Xilenol Orange assay. The mixture was evaporated to reduce the solvent volume. Complexes 12a and 12b were purified from salts by size exclusion chromatography while complexes 12c, 12d and 12e were isolated by precipitation and filtration.

Example 2.3a

Preparation of Compound 12a

[[6-[Bis[(carboxy)methyl]amino]-6-[5-(dibutylamino)-5-oxopent-1-yl]-tetrahydro-1H-1,4-diazepine-1,4(5H)-diacetate(4-)]gadolinate(1-)]sodium salt Starting material: Compound 11a (0.800 g; 1.16 mmol);
Compound 12a: (0.715 g; 0.97 mmol); Yield: 84%
Analytical data:
HPLC-ELSD: ELSD 93.9% (area %)
Mr: 735.89 (C26H42GdNaN4O9)
KF: 10.01%
MS is compatible with the structure

Example 2.3b

Preparation of Compound 12b

[[6-[Bis[(carboxy)methyl]amino]-6-[5-(dihexylamino)-5-oxopent-1-yl]-tetrahydro-1H-1,4-diazepine-1,4(5H)-diacetate(4-)]gadolinate(1-)]sodium Starting material: Compound 11b (1.28 g; 1.49 mmol);
Compound 12b (0.550 g; 0.70 mmol); Yield: 47%
Analytical data:
HPLC-ELSD: ELSD 98.0% (area %)
Mr: 790.99 (C30H50GdN4NaO9)
KF: 12.63%
MS is compatible with the structure

Example 2.3c

Preparation of Compound 12c

[[6-[Bis[(carboxy)methyl]amino]-6-[5-(dioctylamino)-5-oxopent-1-yl]-tetrahydro-1H-1,4-diazepine-1,4(5H)-diacetate(4-)]gadolinate(1-)]sodium Starting material: Compound 11c (1.14 g; 1.27 mmol);
Compound 12c (1.03 g; 1.22 mmol); Yield: 96%
Analytical data:
HPLC-ELSD: ELSD 100.0% (area %)
Mr: 847.10 (C34H58GdN4NaO9)
KF: 5.07%
MS is compatible with the structure

Example 2.3d

Preparation of Compound 12d

[[6-[Bis[(carboxy)methyl]amino]-6-[5-(didecylamino)-5-oxopent-1-yl]-tetrahydro-1H-1,4-diazepine-1,4(5H)-diacetate(4-)]gadolinate(1-)]sodium Starting material: Compound 11d (1.1 g; 1.48 mmol);
Compound 12d (1.12 g; 1.24 mmol); Yield 90%
Analytical data:
HPLC-ELSD: ELSD 94.6% (area %)

Mr: 903.20 (C38H66GdN4NaO9)
MS is compatible with the structure

Example 2.3e

Preparation of Compound 12e

[[6-[Bis[(carboxy)methyl]amino]-6-[5-(didodecylamino)-5-oxopent-1-yl]-tetrahydro-1H-1,4-diazepine-1,4(5H)-diacetate(4-)]gadolinate(1-)]sodium Starting material: Compound 11e (1.10 g; 1.37 mmol);
Compound 12e (1.02 g; 1.06 mmol); Yield: 78%
Analytical data:
HPLC-ELSD: ELSD 94.3% (area %)
Mr: 959.31 (C42H74GdN4NaO9).
MS is compatible with the structure

Example 3

Preparation of Compound 21

6-[Bis[2-(1,1-dimethylethoxy)-2-oxoethyl]amino]-6-[(1R,4R)-4-carboxycyclohexane-1-yl]tetrahydro-1H-1,4-diazepine-1,4(5H)-diacetic acid bis(1,1-dimethylethyl)ester Compound 21 is prepared according to the Scheme 5:

Scheme 5

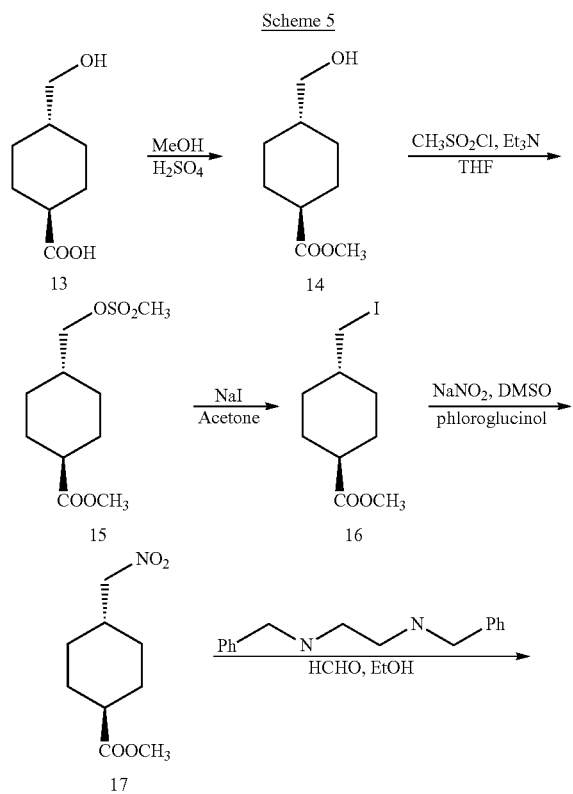

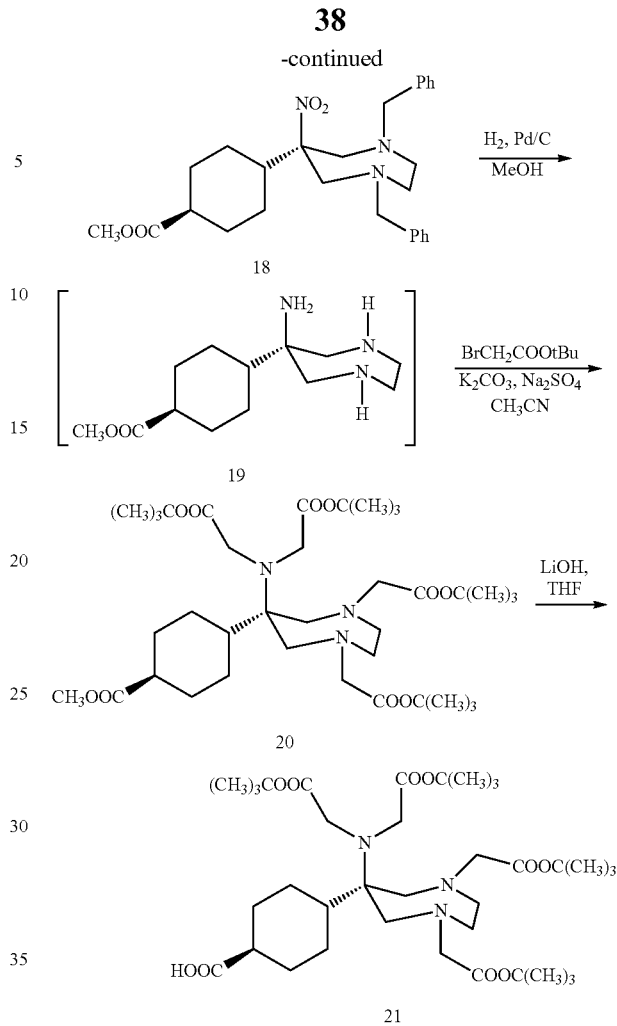

Example 3a

Preparation of Compound 14

(1R,4R)-4-(Hydroxymethyl)cyclohexanecarboxylic acid methyl ester

Concentrated $H_2SO_4$ (15 mL) was added to a solution of trans-4-hydroxymethylcyclohexane carboxylic acid 13 (15 g; 94.8 mmol) in MeOH (300 mL) then the reaction mixture was stirred and refluxed for 4 h. The solution was concentrated under reduced pressure and basified by addition of aq. $NH_4OH$; the white solid was filtered off and the mother liquor was extracted with EtOAc (3×70 mL). The combined organic layers were washed with saturated aq. NaCl, dried ($Na_2SO_4$) and evaporated at reduced pressure to give 14 as a yellow liquid (17.26 g) that was employed in the following reaction without further purification.

Quantitative yield.
Analytical data:
Mr: 172.22 (C9H16O3)
$^1H$- and $^{13}C$-NMR and MS are compatible with the structure

Example 3b

Preparation of Compound 15

(1R,4R)-4-(Methylsulfonyloxy)methyl]cyclohexanecarboxylic acid methyl ester

To a solution of compound 14 (17.26 g) in THF (450 mL) stirred at 0° C. was added triethylamine (39.4 mL; 284.5 mmol) followed by methanesulfonyl chloride (14.9 mL; 151.7 mmol). The mixture was stirred at 0° C. for additional 10 min then the reaction mixture was stirred at room temperature for 2 h. The reaction mixture was filtered through a Celite (0.01-0.04 mm) bed that was then washed with fresh THF; the resulting solution was evaporated under reduced pressure to give 15 as a yellow oil (30.95 g) that was employed in the following reaction without further purification.
Quantitative yield.
Analytical data:
Mr: 250.30 (C10H18O5S)
$^1$H- and $^{13}$C-NMR and MS are compatible with the structure

Example 3c

Preparation of Compound 16

(1R,4R)-4-(Iodomethyl)cyclohexanecarboxylic acid methyl ester

A solution of compound 15 (30.95 g) and sodium iodide (42.64 g; 284.5 mmol) in acetone (450 mL) was stirred at room temperature for 2 h then refluxed for 3.5 h. After 60 h at room temperature additional NaI (5 g; 17.7 mmol) was added and the solution was refluxed for further 7 hours. The reaction was monitored by TLC. The solvent was evaporated under reduced pressure and the yellow residue was treated with diethyl ether; the insoluble salts were filtered off and washed with fresh diethyl ether. The filtrate was evaporated and the dark yellow crude was purified by flash chromatography to give 16 as a yellow liquid (22.43 g; 79.5 mmol).
Yield: 84%
Analytical data:
Mr: 282.12 (C9H15IO2)
$^1$H- and $^{13}$C-NMR and MS are compatible with the structure

Example 3d

Preparation of Compound 17

(1R,4R)-4-(Nitromethyl)cyclohexanecarboxylic acid methyl ester

Compound 16 (21.92 g; 77.7 mmol) was added to a solution of sodium nitrite (10.72 g; 155.4 mmol) and phloroglucinol (10.78 g; 85.4 mmol) in DMSO (1 L) and the solution was stirred at room temperature under a N$_2$ atmosphere for 48 h. The reaction mixture was diluted with H$_2$O (3 L) and extracted with Et$_2$O. The organic layer was dried (Na$_2$SO$_4$) and evaporated to give a crude that was purified by flash chromatography. Compound 17 (10.35 g; 51.4 mmol) was afforded as a pale yellow liquid. Yield: 66%
Analytical data:
HPLC: 97.9% (HPLC Area %)
Mr: 201.22 (C9H15NO4)
$^1$H- and $^{13}$C-NMR and MS are compatible with the structure

Example 3e

Preparation of Compound 18

6-[(1R,4R)-4-(methoxycarbonyl)cyclohexane-1-yl]-6-nitro-1,4-bis(phenylmethyl)-tetrahydro-1H-1,4-diazepine A suspension of N,N'-dibenzylethylenediamine diacetate (18.29 g; 50.7 mmol) in EtOH (400 mL) was stirred at 60° C. until a clear solution was obtained; paraformaldehyde (4.57 g; 152.2 mmol) was added and the suspension was heated at 80° C. for 1.5 h to give a dark orange clear solution. A solution of compound 17 (10.21 g; 50.7 mmol) in EtOH was added dropwise and the final solution was stirred at 80° C. for 6 h; the reaction was monitored by HPLC. After 15 h at room temperature, the resulting precipitate was filtered, washed with EtOH and dried under vacuum to give 18 as a white solid (17.88 g; 38.4 mmol).
Yield: 76%
Analytical data:
HPLC: 99.6% (HPLC Area %)
Mr: 465.59 (C27H35N3O4)
$^1$H- and $^{13}$C-NMR and MS are compatible with the structure.

Example 3f

Preparation of Compound 19

6-Amino-6-[(1R,4R)-4-(methoxycarbonyl)cyclohexane-1-yl]-tetrahydro-1H-1,4-diazepine A suspension of compound 18 (17.88 g; 38.4 mmol) in THF (200 mL) was stirred at 40° C. until a clear solution was obtained then the solution was diluted with MeOH (150 mL). A suspension of 5% Pd/C (10.66 g) in MeOH (50 mL) was added and the mixture was hydrogenated at 40° C. for 11 h at ambient pressure. The catalyst was filtered off and the solution was evaporated to give 19 as a greenish oil (9.57 g; 37.4 mmol). This product was used in the following without purification.
Yield: 98%
Analytical data:
Mr: 255.36 (C13H25N3O2)
$^1$H- and $^{13}$C-NMR and MS are compatible with the structure.

Example 3g

Preparation of Compound 20

6-[Bis[2-(1,1-dimethylethoxy)-2-oxoethyl]amino]-6-[(1R,4R)-4-(methoxycarbonyl)-cyclohexane-1-yl]tetrahydro-1H-1,4-diazepine-1,4(5H)-diacetic acid bis(1,1-dimethylethyl)ester The compound 19 (9.52 g; 37.3 mmol) was dissolved in CH$_3$CN (400 mL) then freshly grounded K$_2$CO$_3$ (23.19 g; 167.8 mmol) and Na$_2$SO$_4$ (15.88 g; 111.8 mmol) were added. t-butyl bromoacetate (24.6 mL; 167.8 mmol) was added and the orange mixture was stirred at 80° C. for 16 h. The salts were filtered off, and the filtrate was evaporated to residue that was dissolved in EtOAc (200 mL) and the solution washed with H$_2$O (3×70 mL) and saturated aq. NaCl (70 mL). The organic phase was dried (Na$_2$SO$_4$), filtered and evaporated. The crude (27.36 g) was purified with flash chromatography to give 20 as a pale yellow oil (5.34 g; 7.5 mmol).

Yield: 20%

Analytical data:

Mr: 711.93 (C37H65N3O10)

$^1$H- and $^{13}$C-NMR and MS are compatible with the structure

Example 3h

Preparation of Compound 21

6-[Bis[2-(1,1-dimethylethoxy)-2-oxoethyl]amino]-6-[(1R,4R)-4-carboxy-cyclohexane-1-yl]tetrahydro-1H-1,4-diazepine-1,4(5H)-diacetic acid bis(1,1-dimethylethyl)ester 2N NaOH (7.12 mL; 14.2 mmol) was added to a solution of compound 20 in i-PrOH (100 mL) stirred at room temperature then H$_2$O (5.5 mL) was added until a homogeneous mixture was obtained. The solution was stirred for 5.5 h at room temperature, as the reaction was not completed, the solution was stored at −20° C. for 15 h. The temperature was allowed to raise to room temperature and the reaction mixture was stirred for further 3 h. The pH was corrected to 7 with 2N HCl (7.12 mL) and the solution was evaporated under reduced pressure at room temperature. The residue was suspended in H$_2$O (80 mL), acidified with 2N HCl (7.12 mL) and extracted with EtOAc. The organic layer was dried (Na$_2$SO$_4$) and evaporated to give 21 as a white solid (4.5 g; 6.45 mmol).

Yield: 90%

Analytical data:

Mr: 697.91 (C36H63N3O10).

$^1$H- and $^{13}$C-NMR and MS are compatible with the structure.

Example 4

Preparation of Compounds 25 (a-c)

Compounds 25 (a-c) are prepared according to the Scheme 6:

Scheme 6

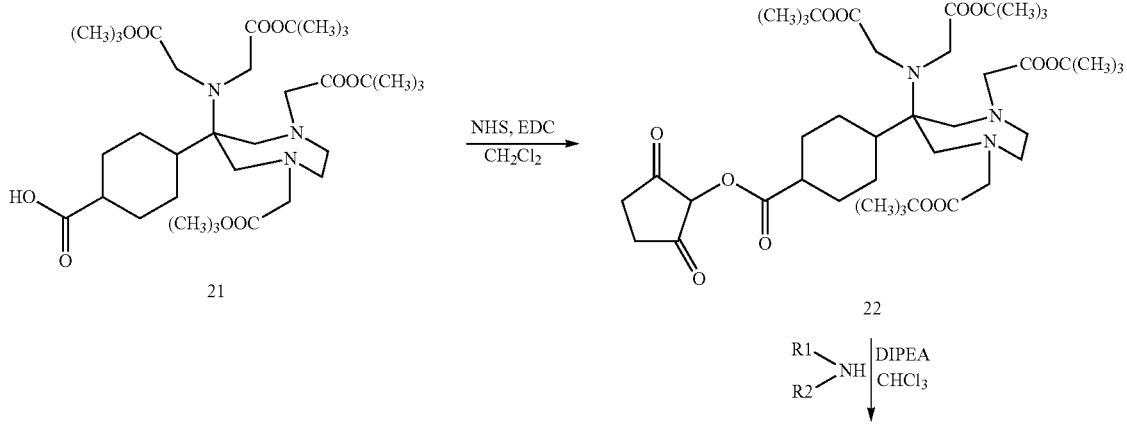

23a: R$_1$ = R$_2$ = CH$_3$(CH$_2$)$_9$
23b: R$_1$ = R$_2$ = CH$_3$(CH$_2$)$_7$
23c: R$_1$ = H

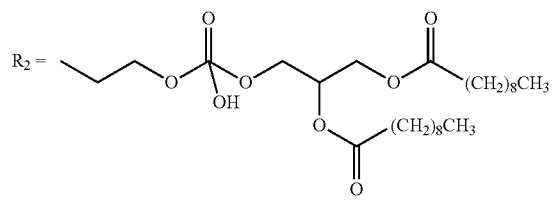

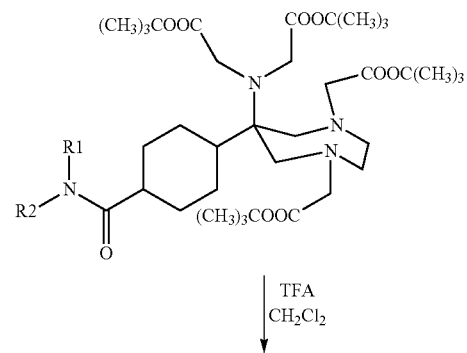

24a: from 23a
24b: from 23b
24c: from 23c

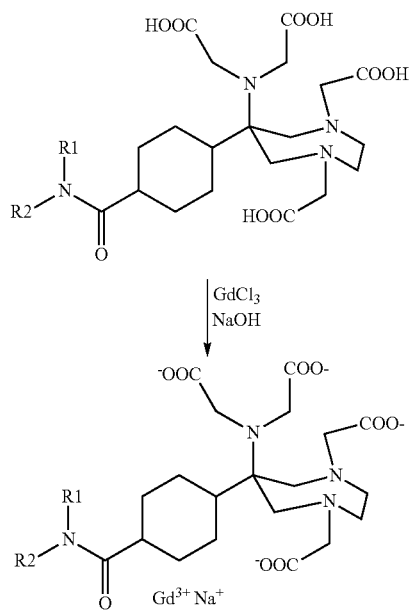

25a: from 24a
25b: from 24b
25c: from 24c

Example 4.1

Preparation of compound 22

6-[Bis[2-(1,1-dimethylethoxy)-2-oxoethyl]amino]-6-[(1R,4R)-4-[[(2,5-dioxopirrolidin-1-yl)oxy]carbonyl]cyclohexane-1-yl]tetrahydro-1H-1,4-diazepine-1,4(5H)-diacetic acid bis(1,1-dimethylethyl)ester NHS (0.27 g; 2.3 mmol) was added to a solution of 21 (1.09 g; 1.6 mmol) in $CH_2Cl_2$ (50 mL) stirred at 0° C., then a solution of EDC (0.45 g; 2.3 mmol) in $CH_2Cl_2$ (50 mL) was added dropwise. The reaction mixture was stirred at room temperature for 49 h; the reaction was monitored by TLC. The final solution was washed with $H_2O$ (3×40 mL) and the organic layer was dried ($Na_2SO_4$) and evaporated to give 22 as a solid (1.35 g) that was used in the next step without further purification. Quantitative Yield.

Example 4.2

Preparation of Compounds 23(a-c). General Procedure

The corresponding amine (1-1.3 eq) was added to a solution of compound 22 (1 eq) in $CHCl_3$ (concentration 2%) followed by addition of DIPEA (1.7 eq). The mixture was stirred at room temperature for 64-72 h. As the reaction solution became neutral, additional DIPEA (1.7 eq) was added and the reaction mixture was stirred at room temperature for further 2-21 h. The reaction mixture was then washed subsequently with $H_2O$ (35 mL), with diluted aq. HCl until pH of washing was acid (3×40 mL) and with $H_2O$ (35 mL). The organic phase was dried ($Na_2SO_4$) and evaporated to give a viscous yellowish crude that was purified by flash chromatography to give 23(a-c) as a yellow oil, according to the following data:

Example 4.2a

Preparation of Compound 23a

6-[Bis[2-(1,1-dimethylethoxy)-2-oxoethyl]amino]-6-[(1R,4R)-4-[(didecylamino)-carbonyl]cyclohexane-1-yl]tetrahydro-1H-1,4-diazepine-1,4(5H)-diacetic acid bis(1,1-dimethylethyl)ester Starting materials: Compound 22 (1.18 g; 1.48 mmol); didecylamine (0.44 g; 1.48 mmol)

Compound 23a (075 g; 0.77 mmol). Yield: 52%

Mr: 977.46 ($C_{56}H_{104}N_4O_9$)

$^1$H- and $^{13}$C-NMR and MS are compatible with the structure

Example 4.2b

Preparation of Compound 23b

6-[Bis[2-(1,1-dimethylethoxy)-2-oxoethyl]amino]-6-[(1R,4R)-4-[(dioctylamino)-carbonyl]cyclohexane-1-yl]tetrahydro-1H-1,4-diazepine-1,4(5H)-diacetic acid bis(1,1-dimethylethyl)ester Starting materials: Compound 22 (0.74 g; 0.93 mmol); dioctylamine (0.74 g; 0.93 mmol)

Compound 23b (0.30 g; 0.33 mmol). Yield: 35%

Mr: 921.35 ($C_{52}H_{96}N_4O_9$)

$^1$H- and $^{13}$C-NMR and MS are compatible with the structure.

Example 4.2c

Preparation of Compound 23c

6-[Bis[2-[(1,1dimethyl)ethoxy]-2-oxoethyl]amino]-6-(1R,4R)-4-[[[(7R)-4-hydroxy-4-oxido-10-oxo-7-[(1-xodecyl)oxy]-3,5,9-trioxa-4-phosphanonadec-1-yl]amino]-carbonyl]cyclohexane-1-yl]tetrahydro-1H-1,4-diazepine-1,4(5H)-diacetic acid bis[(1,1-dimethyl)ethyl]ester Starting materials: Compound 22 (1.35 g; 1.56 mmol); 1,2-didecanoyl-sn-glycero-3-phosphoethanolamine (0.81 g; 1.56 mmol)
Compound 23c (0.84 g; 0.70 mmol). Yield: 45%
Mr: 1203.54 ($C_{61}H_{111}N_4O_{17}P$)
$^1H$- and $^{13}C$-NMR and MS are compatible with the structure

Example 4.3

Preparation of Compounds 24(a-c). General Procedure

TFA (6 eq) was added dropwise to a solution of compound 23(a-c) (1 eq) in $CH_2Cl_2$ (50 mL) stirred at 0° C. The reaction mixture was stirred for 1 hour at room temperature then evaporated to residue that was dissolved with fresh TFA (350 eq); the solution was then stirred at room temperature for 24-28 h. The reaction was monitored by ESI-MS. The TFA was evaporated and the residue was treated with $iPr_2O$ (40-60 mL) to give a white solid that was isolated by centrifugation and dried (at reduced pressure and at 30° C. in the presence of NaOH pellets) to give 24(a-c) according to the following data:

Example 4.3a

Preparation of Compound 24a

6-[Bis(carboxymethyl)amino]-6-[(1R,4R)-4-[(didecylamino)-carbonyl]cyclohexane-1-yl]tetrahydro-1H-1,4-diazepine-1,4(5H)diacetic acid Starting material: Compound 23a (0.75 g; 0.77 mmol)
Compound 24a (0.41 g; 0.54 mmol); Yield: 70%
Analytical data:
HPLC-ELSD: 94.1% (HPLC Area %)
Mr: 753.03 ($C_{40}H_{72}N_4O_9$)
Complexometric Titer: (0.001 M $GdCl_3$): 81.7%
$^1H$- and $^{13}C$-NMR and MS are compatible with the structure.

Example 4.3b

Preparation of Compound 24b

6-[Bis(carboxymethyl)amino]-6-[(1R,4R)-4-[(dioctylamino)-carbonyl]cyclohexane-1-yl]tetrahydro-1H-1,4-diazepine-1,4(5H)-diacetic acid Starting material: Compound 23b (0.30 g; 0.33 mmol)
Compound 24b (0.21 g; 0.30 mmol); Yield: 90%
Analytical data:
HPLC-ELSD: 98% (HPLC Area %)
Mr: 696.92 ($C_{36}H_{64}N_4O_9$)
Complexometric Titer: (0.001 M $GdCl_3$): 77%
$^1H$- and $^{13}C$-NMR and MS are compatible with the structure

Example 4.3c

Preparation of Compound 24c

6-[-[Bis(carboxymethyl)amino]-6-[(1R,4R)-4-[[[(7R)-4-hydroxy-4-oxido-10-oxo-7-[(1-oxodecyl)oxy]-3,5,9-trioxa-4-phosphanonadec-1-yl]amino]-carbonyl]-cyclohexane-1-yl]tetrahydro-1H-1,4-diazepine-1,4(5H)-diacetic add Starting material: Compound 23c (0.84 g; 0.70 mmol)
Compound 24c (0.67 g; 0.69 mmol); Yield: 98%
Analytical data:
HPLC-ELSD: 96.2% (HPLC Area %) [13]
Mr: 979.11 ($C_{45}H_{79}N_4O_{17}P$)
Complexometric Titer: (0.001 M $GdCl_3$): 96.9%
$^1H$- and $^{13}C$-NMR and MS are compatible with the structure.

Example 4.4

Preparation of Compounds 25(a-c). General Procedure

The titled compounds were prepared according to the procedure described in Example 2.3.

Example 4.4a

Preparation of Compound 25a

[[6-[Bis(carboxymethyl)amino]-6-[(1R,4R)-4-[(didecylamino)-carbonyl-cyclohexane-1-yl]tetrahydro-1H-1,4-diazepine-1,4(5H)diacetate(4-)]gadolinate(1-)]sodium Starting material: Compound 24a (0.32 g; 0.43 mmol)
Compound 25a (0.33 g; 0.35 mmol); Yield: 83%
Analytical data:
HPLC-ELSD: 95.2% (% HPLC Area) [13]
Mr: 929.24 ($C_{40}H_{68}GdN_4\ NaO_9$)
TGA: 5.7%
MS is compatible with the structure.

Example 4.4b

Preparation of Compound 25b

[6-[Bis(carboxymethyl)amino]-6-[(1R,4R)-4-[(dioctylamino)-carbonyl]-cyclohexane-1-yl]tetrahydro-1H-1,4-diazepine-1,4(5H)diacetate(4-)]gadolinate(1-)]sodium Starting material: Compound 24b (0.18 g; 0.26 mmol)
Compound 25b (46 mg; 0.05 mmol); Yield:19%
Analytical data:
Mr: 873.13 ($C_{36}H_{60}GdN_4\ NaO_9$)
MS is compatible with the structure.

Example 4.4c

Preparation of Compound 25c

[6-[-[Bis(carboxymethyl)amino]-6-[(1R,4R)-4-
[[[(7R)-4-hydroxy-4-oxido-10-oxo-7-[(1-oxodecyl)
oxy]-3,5,9-trioxa-4-phosphanonadec-1-yl]amino]-
carbonyl]-cyclohexane-1-yl]tetrahydro-1H-1,4-
diazepine-1,4(5H)-diacetate(5)]gadolinate(2-)]
disodium Starting material: Compound 24c (0.35 g; 0.36 mmol)
Compound 25c (0.31 g; 0.27 mmol); Yield: 77%
Analytical data:
Mr: 1155.32 (C45H75GdN4 NaO17P)
TGA: 9%
KF: 11.6%.
MS is compatible with the structure

TABLE I $r_{1p}$ (mM$^{-1}$s$^{-1}$) for different Diazepine complexes,
and for Gd-DOTA, Gd-HP-DO3A, Gd-BT-DO3A and Gd-BOPTA,
determined in different media at 0.47T, 25° C.

|  | Water | HSA 4% $r_{1p}$ (mM$^{-1}$s$^{-1}$) | Human plasma |
|---|---|---|---|
| 12a | 14.0 | 20.0 | 15.8 |
| 12b | 13.0 | 31.5 | 33.7 |
| 12c | 13.3 | 54.2 | 50.2 |
| 12d | 23.5 | 46.7 | 45.2 |
| 12e | 33.4 | 40.4 | 36.2 |
| 9a | 11.7 | 32.7 | 34.2 |
| 9b | 16.7 | 32.0 | 32.5 |
| 9c | 28.3 | 26.7 | 30.6 |
| 25a | 23.9 | 45.8 | 41.1 |
| 25b | 14.6 | 41.0 | 39.1 |
| 25c | 14.7 | 40.2 | 43.0 |
| Gd-DOTA[a] | 3.61 | 4.11 | 4.51 |
| Gd-HP-DO3A[b] | 3.32 | 3.85 | 4.80 |
| Gd-BT-DO3A[c] | 3.75 | 4.31 | 5.76 |
| Gd-BOPTA[d] | 4.6 | 8.9 | 8.7 |

[a]Gd-DOTA: Gadoterate meglumine [[1,4,7,10-tetraazacyclododecane-1,4,7,10-tetraacetato(4-)]gadolinate(1-)] meglumine
[b]Gd-HP-DO3A: Gadoteridol [10-(2-hydroxyprop-1-yl)-1,4,7,10-tetraazacyclododecane-1,4,7-triacetato(3-)]gadolinium
[c]Gd-BT-DO3A: Gadobutrol [[10-[(2R,3S)-2,3-dihydroxy-1-(hydroxymethyl)prop-1-yl]-1,4,7,10-tetraaza-cyclododecane-1,4,7-triacetato(3-)]gadolinium
[d]Gd-BOPTA: Gadobenate dimeglumine [[4-(carboxy)-5,8,11-tris(carboxymethyl)-1-phenyl-2-oxa-5,8,11-triazatridecan-13-oato(5-)]gadolinate(2-)]dimeglumine For all the compounds, longitudinal relaxation times (T1) at 20 MHz and at 25° C. on a mq20 Minispec instrument (Bruker Biospin, Germany) were measured in water, human serum albumin at physiological concentration and human plasma. Millimolar relaxivity $r_{1p}$ was thus determined from T1 measurements using the following equation:

$$R^i{}_{1obs} = 1/T^{i,j}{}_{1obs} = r^{i,j}{}_{1p} \cdot [Gd^{3+}] + 1/T^j{}_1$$

wherein $R^i{}_{1obs}$ is the observed relaxation time of the selected contrast agent, $T_{1obs}$ is the observed longitudinal relaxation time of the solution and the indexes i and j relate to the contrast agent and to the medium respectively.

The above $r_{1p}$ values clearly demonstrate that the compounds of the present invention are endowed with a high relaxivity, as measured in water, HSA and even in plasma. In particular, when compared to known contrast agents broadly used in MRI analysis, such as Gd-DOTA, Gd-BOPTA and Gd-BT-DO3A, the present derivatives show a remarked increased relaxivity, thus rendering them particularly suitable as MRI contrast agents.

TABLE II

Stability at 37° C. of different diazepine complexes
determined through $r_{1p}$ (mM$^{-1}$ s$^{-1}$) measurement
in different media at 0.47T, 25° C.

| 12d | $T_0$ | 2 h $r_{1p}$ (mM$^{-1}$s$^{-1}$) | 5 h |
|---|---|---|---|
| Water | 23.5 | 20.4 | 15.8 |
| HSA 4% | 46.7 | — | 40.9 |
| Human plasma | 45.2 | 39.2 | 34.7 |

| 12e | $T_0$ | 2 h $r_{1p}$ (mM$^{-1}$s$^{-1}$) | 4 h |
|---|---|---|---|
| Water | 33.4 | 31.3 | 30.4 |
| Human plasma | 36.2 | 35.2 | 32.3 |

| 9a | $T_0$ | 2 h $r_{1p}$ (mM$^{-1}$s$^{-1}$) | 5 h |
|---|---|---|---|
| Water | 11.7 | — | 11.1 |
| HSA 4% | 32.7 | — | 30.8 |

| 9b | $T_0$ | 1 h $r_{1p}$ (mM$^{-1}$s$^{-1}$) | 4 h |
|---|---|---|---|
| Water | 16.7 | 15.9 | 15.5 |
| Human plasma | 32.5 | 30.9 | 28.3 |

| 25a | $T_0$ | 2 h $r_{1p}$ (mM$^{-1}$s$^{-1}$) | 5 h |
|---|---|---|---|
| Water | 23.9 | — | 23.4 |
| HSA 4% | 45.8 | — | 40.4 |

Table II shows that the relaxivity values $r_{1p}$ of the amphiphilic complexes of the invention remain substantially stable over the time, thus providing a favourable lasting time during the experiment. In its turn, this means that the present amphiphilic complexes can be administered and detected during MRI experiments allowing a clear and exhaustive analysis of the image over a suitable frame of time.

The invention claimed is:
1. A compound of formula (I):

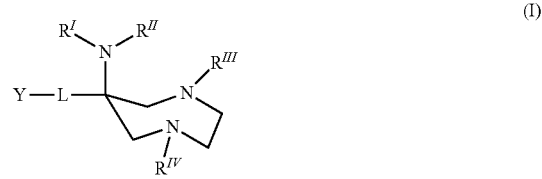

or a pharmaceutically acceptable salt thereof,
wherein:
Y is a group of formula: Y'—NH— or (Y')$_2$—N—, wherein Y' is the same or different and is selected from the group consisting of: a linear or branched saturated or unsaturated C$_1$-C$_{20}$ alkyl group; and a C$_1$-C$_{10}$ alkyl group interrupted by one or more atoms or groups selected from: —P— and —O—(HO—P=O)—O—, said C$_1$-C$_{10}$ alkyl group being optionally substituted by one or more groups selected from: hydroxy —OH, carboxy —COOR$_1$, oxycarbonyl-(C$_1$-C$_{30}$)alkyl and oxycarbonyl-(C$_2$-C$_{30}$)alkertyl group and wherein R$_1$ is selected from: hydrogen H and a linear or branched C$_1$-C$_{10}$ alkyl group;
L is a bivalent linker selected from: aliphatic C$_3$-C$_{10}$ cyclic or heterocyclic ring, linear or branched C$_1$-C$_6$ alkyl group and C$_2$-C$_6$ alkenyl or alkynyl group, optionally substituted and optionally interrupted with a group or atom selected from: carbonyl —C=O, thiocarbonyl —C=S, amino —NR1-, carboxy —COO—, oxycarbonyl —OCO—, amido —NR1CO— or —CONR1-, oxygen —O— and sulphur —S—, wherein $R_1$ is as above defined;

$R^{I-IV}$ are each independently selected from: hydrogen H, carboxy —$COOR_1$, and —($C_1$-$C_6$)alkylcarboxy group, wherein $R_1$ is as above defined.

2. The compound of formula (I) according to claim 1, wherein Y has the formula: Y'—NH— and Y' is a linear alkyl group having 5 carbon atoms, interrupted by one or more groups of formula:

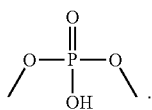

3. The compound according to claim 2, wherein the linear alkyl group is further substituted by 2 oxycarboxyalkyl groups having from 9 to 20 carbon atoms.

4. The compound according to claim 1, wherein Y is selected from:

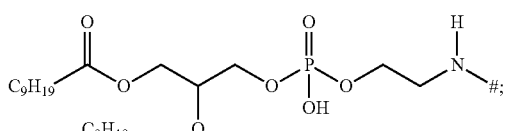

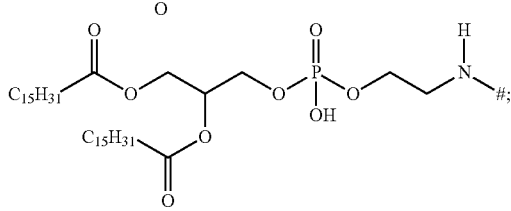

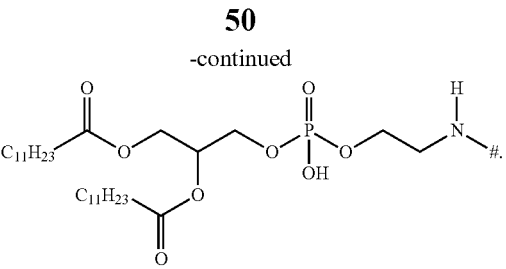

wherein # indicates the point of attachment to the linker L.

5. The compound according to claim 1, wherein Y is a group of formula $(Y')_2$—N— and wherein Y' is a linear or branched $C_1$-$C_{20}$ alkyl group.

6. The compound according to claim 5, wherein Y' is selected from: linear $C_4H_9$, $C_{61}H_{13}$, $C_8H_{17}$, $C_{10}H_{21}$ and $C_{12}H_{25}$.

7. The compound according to claim 5, wherein Y is selected from:

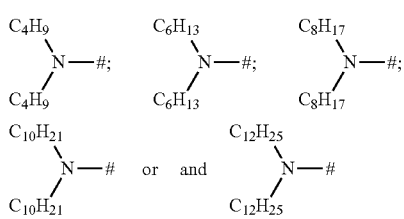

and wherein # indicates the point of attachment to the linker L.

8. The compound according to claim 1 selected from the group consisting of:

(II)

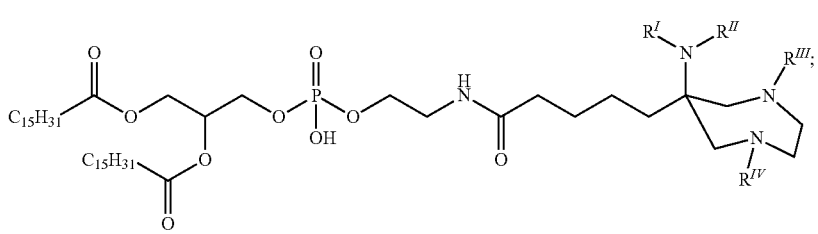

(III)

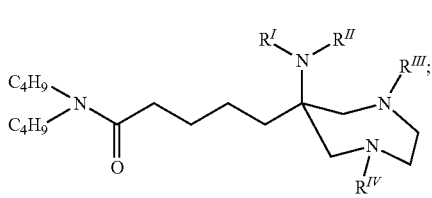

(IV)

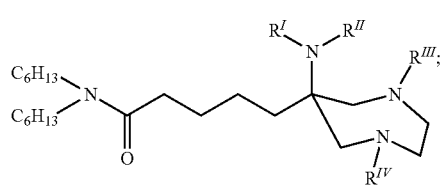

-continued
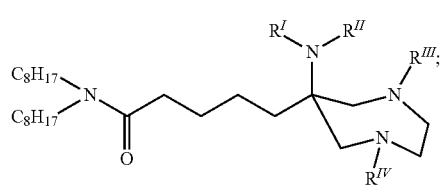
(V)
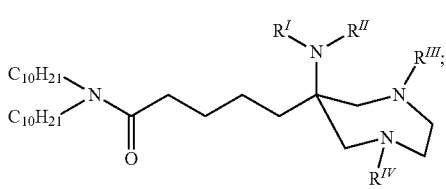
(VI)
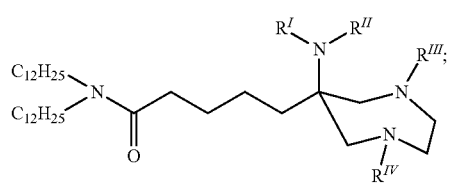
(VII)
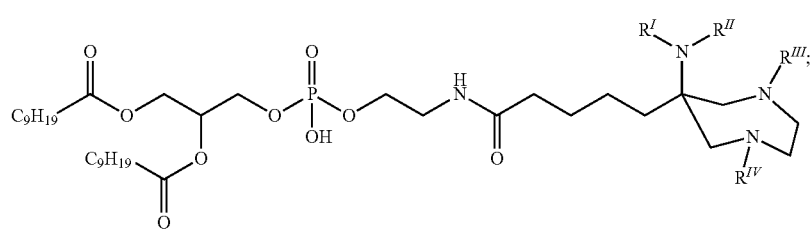
(VIII)
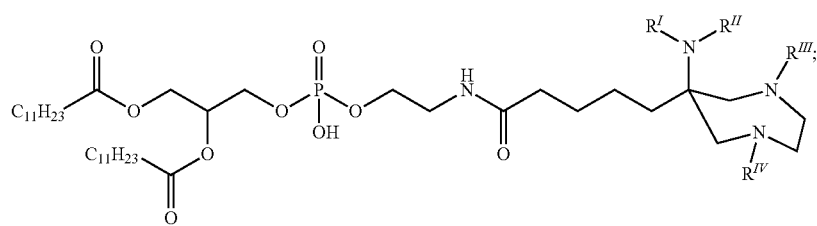
(IX)
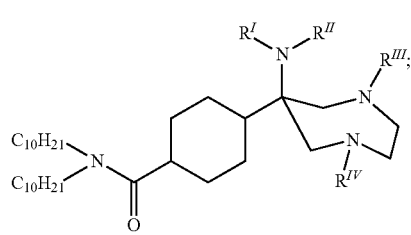
(X)
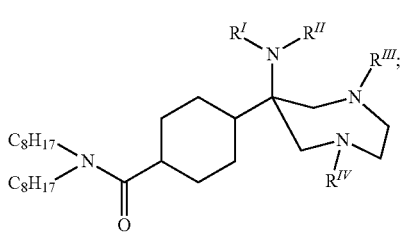
(XI)
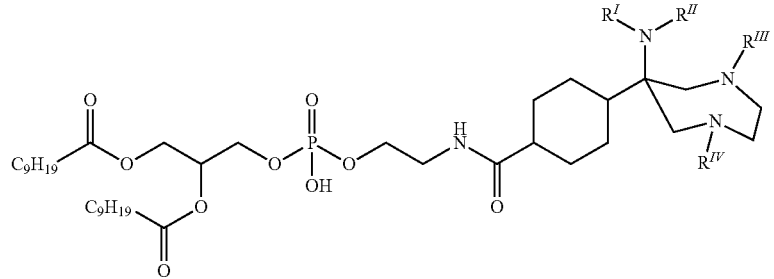
(XII)

9. The compound according to claim 1 selected from:
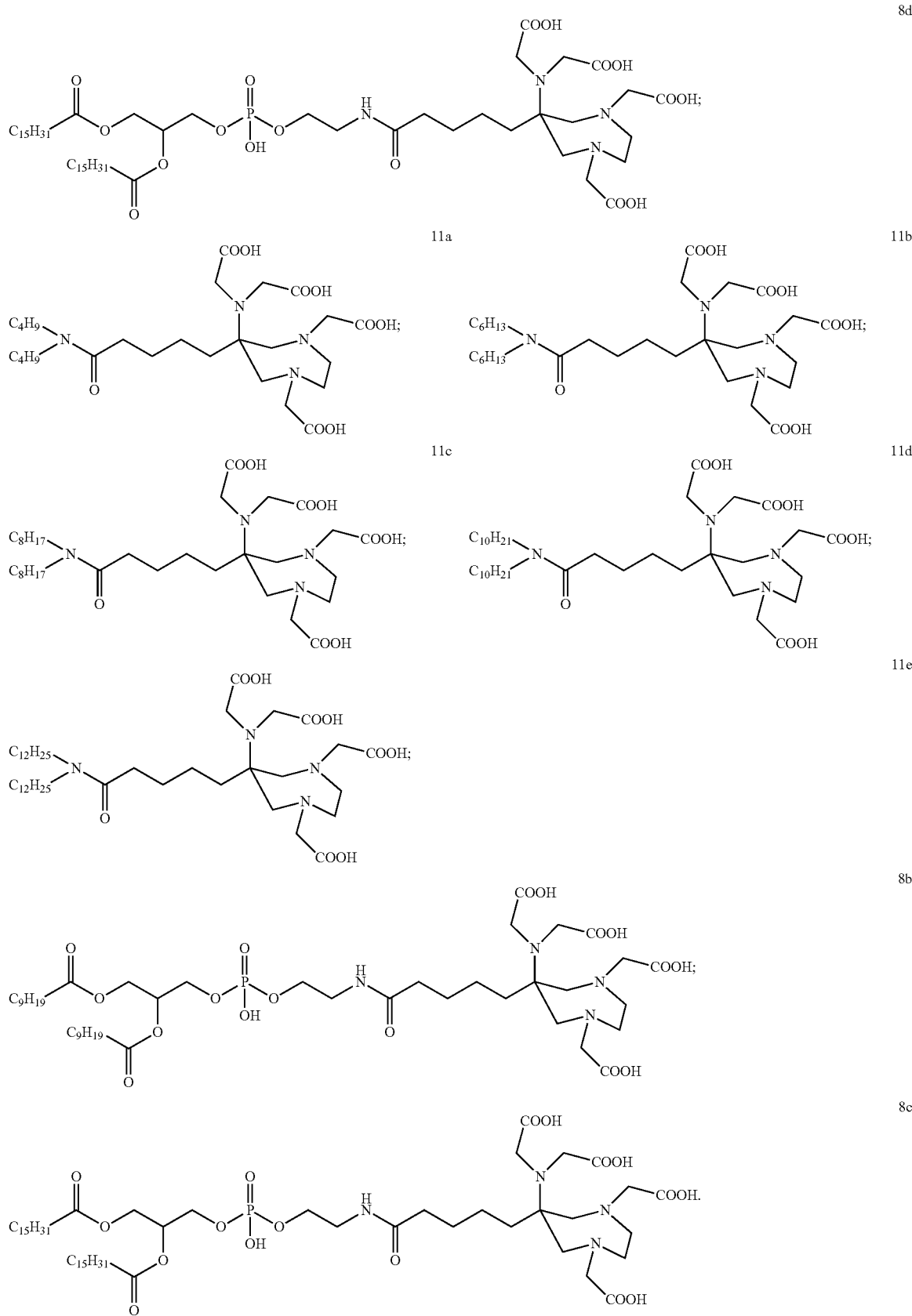

-continued
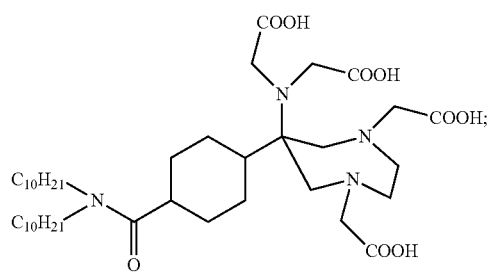
24a
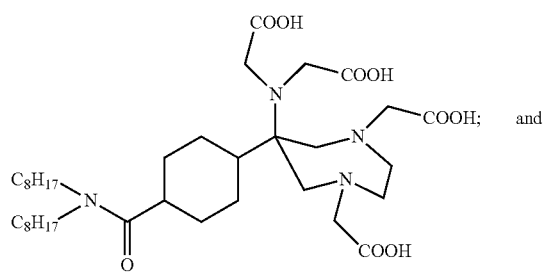
24b
and
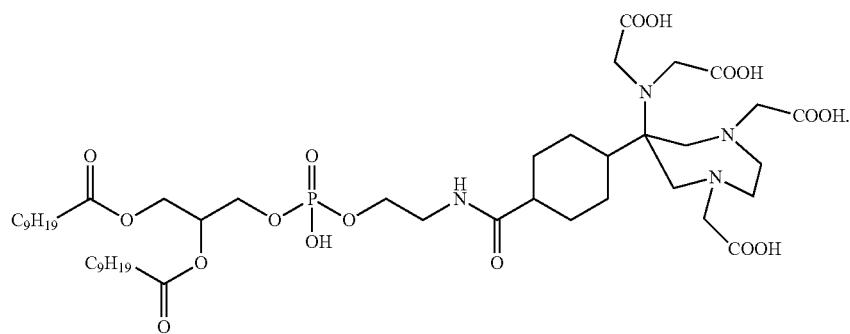
24c
10. A compound according to claim 1, complexed with a paramagnetic metal ion.
11. The compound according to claim 10, wherein the metal ion is $Gd^{3+}$ or $Dy^{3+}$.
12. The compound according to claim 10 selected from:
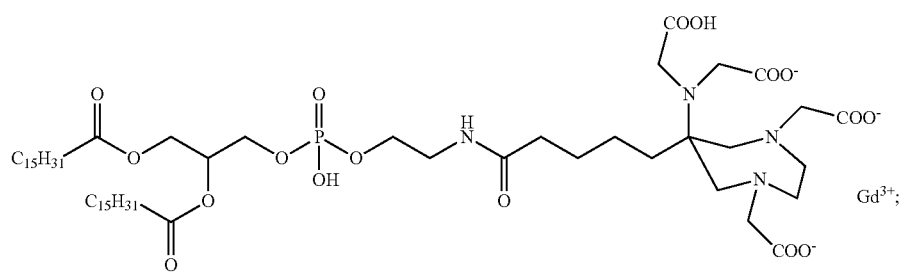
9c
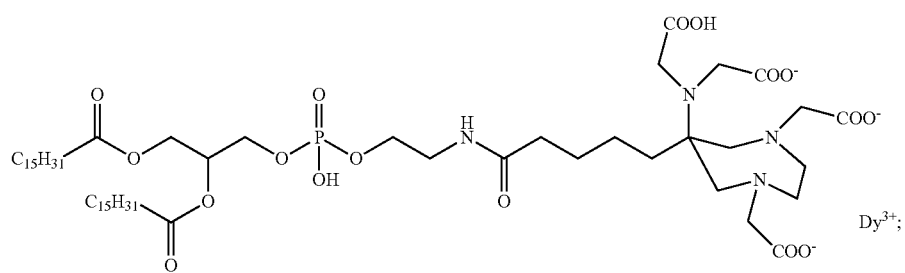
9'c
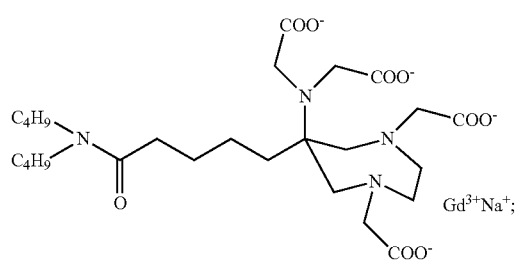
12a
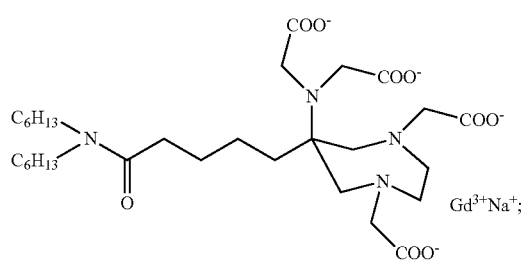
12b -continued
12c
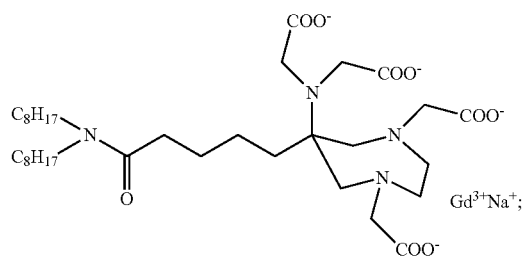
12d
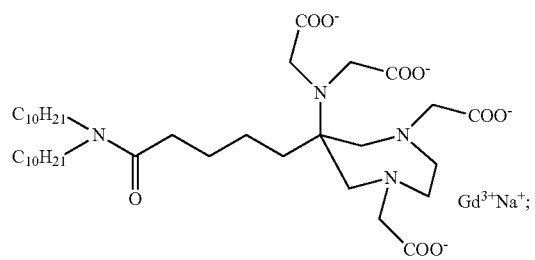
12e
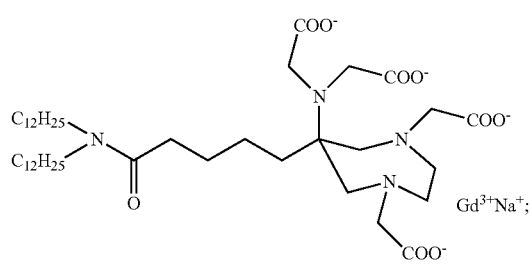
9a
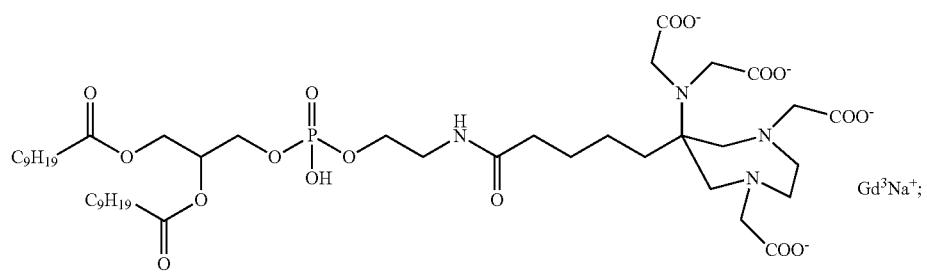
9b
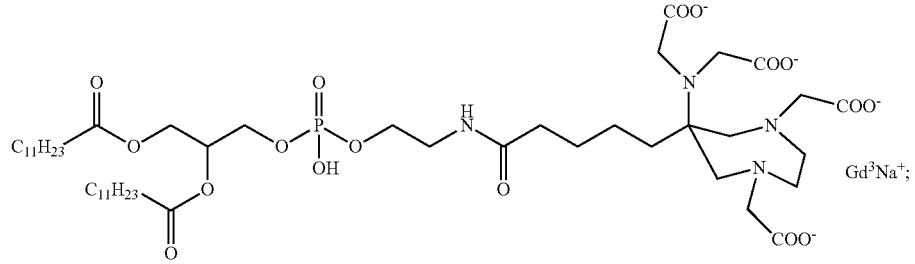
25a
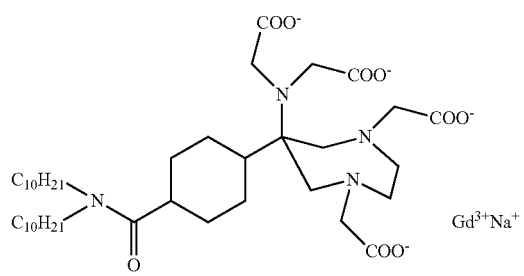
25b
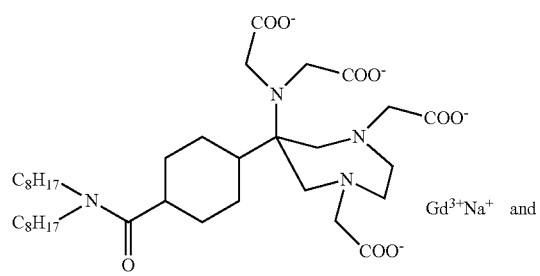

-continued

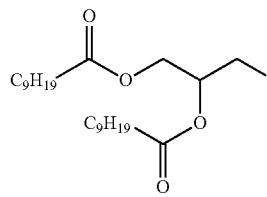 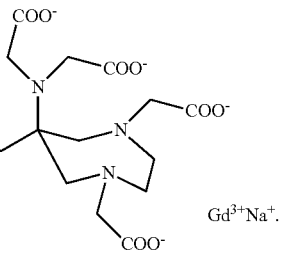

25c

Gd$^{3+}$Na$^+$.

13. A pharmaceutically acceptable composition comprising a paramagnetic complex as defined in claim 10, or a pharmaceutically acceptable salt thereof, in admixture with one or more physiologically acceptable carriers, diluents or excipients.

14. A method for imaging body regions comprising administering to a subject a diagnostically effective amount of the composition according to claim 13 and acquiring MR images.

15. A MRI diagnostic method comprising administering a diagnostically effective amount of a compound according to claim 10 and acquiring MR images.

16. A pharmaceutically acceptable composition comprising a paramagnetic complex as defined in claim 12, or pharmaceutical acceptable salt thereof, in admixture with one or more physiologically acceptable carriers, diluents or excipients.

17. A MRI diagnostic method comprising administering a diagnostically effective amount of a compound according to claim 12 and acquiring MR images.

18. A method for imaging body regions comprising administering to a subject a diagnostically effective amount of the composition according to claim 16 and acquiring MR images.

* * * * *

UNITED STATES PATENT AND TRADEMARK OFFICE
CERTIFICATE OF CORRECTION

PATENT NO. : 9,259,491 B2
APPLICATION NO. : 14/384414
DATED : February 16, 2016
INVENTOR(S) : Beltrami et al.

It is certified that error appears in the above-identified patent and that said Letters Patent is hereby corrected as shown below:

IN THE CLAIMS

Column 48, claim 1, line 62 "$(C_2-C_{30})$alkertyl" should be -- $(C_2-C_{30})$alkenyl --.

Column 50, claim 6, line 19 "$C_{61}H_{13}$" should be -- $C_6H_{13}$ --; claim 7, line 31 "or and" should be -- and --.

Columns 53-54, claim 9, formula 8c, the two portions of the formula reading "$C_{15}H_{31}$" should be -- $C_{11}H_{23}$ --.

Columns 59-60, claim 12, cancel formula 25c and insert the following:

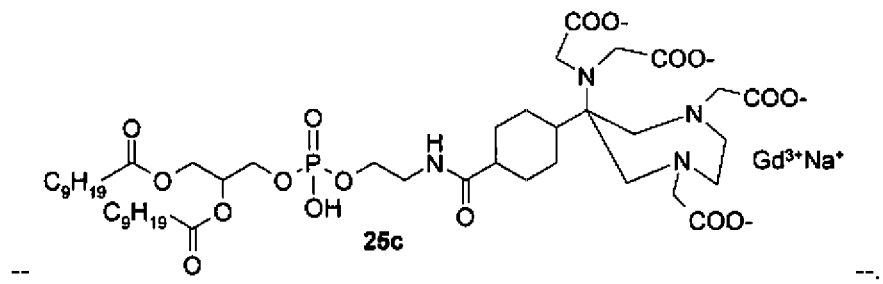

Signed and Sealed this
Twenty-eighth Day of June, 2016

Michelle K. Lee
*Director of the United States Patent and Trademark Office*